US006251654B1

(12) United States Patent
Gordon et al.

(10) Patent No.: US 6,251,654 B1
(45) Date of Patent: Jun. 26, 2001

(54) MODIFIED SMALL RNA VIRUSES

(75) Inventors: Karl Heinrich Gordon, Weston; Terry Nelson Hanzlik, Chapman, both of (AU)

(73) Assignee: Commonwealth Scientific and Industrial Research Organization, Australian Capital Territory (AU)

(*) Notice: Subject to any disclaimer, the term of this patent is extended or adjusted under 35 U.S.C. 154(b) by 0 days.

(21) Appl. No.: 09/194,613

(22) PCT Filed: Jun. 2, 1997

(86) PCT No.: PCT/AU97/00349

§ 371 Date: Jul. 2, 1999

§ 102(e) Date: Jul. 2, 1999

(87) PCT Pub. No.: WO97/46666

PCT Pub. Date: Dec. 11, 1997

(30) Foreign Application Priority Data

May 31, 1996 (AU) .................................................... PO0234

(51) Int. Cl.⁷ ............................... C12N 7/00; C12N 7/04; C12N 7/08; A61K 39/00; A61K 39/29

(52) U.S. Cl. ..................... 435/235.1; 435/236; 435/237; 424/185.1; 424/189.1

(58) Field of Search .................................. 435/235.1, 236, 435/237; 424/189.1, 185.1

(56) References Cited

U.S. PATENT DOCUMENTS

| 5,858,743 | * | 1/1999 | Russell et al. ..................... 435/172.3 |
| 5,871,726 | * | 2/1999 | Henderson et al. ................. 424/93.2 |
| 5,871,727 | * | 2/1999 | Curiel et al. ......................... 424/93.2 |

OTHER PUBLICATIONS

Journal of Molecular Biology, vol. 261, pp. 1–10 (1996) Munshi, et al. "The 2.8 A Structure of a T=4 animal virus and its implications for membrane translocation of RNA."

Journal of General Virology, vol. 76, pp. 799–811 (1995) Hanzlik TN, et al. "Sequence of RNA2 of the *Helicoverpa armigera* stunt virus (Tetraviridae) and bacterial expression of its genes."

Virology, vol. 190, pp. 806–814 (1992) Agrawal DK and Johnson JE "Sequence and analysis of the capsid protein of the capsid protein of *Nudaurelia capensis* virus, and insect virus with T=4 icosahedral symmetry."

* cited by examiner

Primary Examiner—Hankyel T. Park
Assistant Examiner—Stacy S. Brown
(74) Attorney, Agent, or Firm—McDermott, Will & Emery

(57) ABSTRACT

Small RNA viruses and virus-like particles (VLPs) have altered or substituted Ig-like domains so as to modify host cell tropism. The invention also relates to the use of such small RNA viruses and VLPs in insecticidal and medicinal applications.

34 Claims, 13 Drawing Sheets

```
(SEQ ID NO:1)
  1  GTTTTTCTTT CTTTACCAAG TGTGGTAAAA TTTAAACAAA GAAGAAAACC AGGACCGTAA
     CAAAAAGAAA GAAATGGTTC ACACCATTTT AAATTTGTTT CTTCTTTTGG TCCTGGCATT

61  CCCGGCCCTT ACACACCTCG AGTCCGTGAC CACCGGATTA TACGTCGCCC ACCACACGGC
     GGGCCGGGAA TGTGTGGAGC TCAGGCACTG GTGGCCTAAT ATGCAGCGGG TGGTGTGCCG

121  GCCTTTTCCG ACCACTCTCG AGAGTCGTTG GGAGTTTCGT CCGTGACCAC CCGGTTGGCA
     CGGAAAAGGC TGGTGAGAGC TCTCAGCAAC CCTCAAAGCA GGCACTGGTG GGCCAACCGT

81  GTCGACAGAC GCTTCCGGAC CACTAGAACC TCCTCGAGCG ACGCACACAC AGCACACACA
     CAGCTGTCTG CGAAGGCCTG GTGATCTTGG AGGAGCTCGC TGCGTGTGTG TCGTGTGTGT
                                                    p17 start
 +1                                                 (SEQ ID NO:2)M  S  E  H  T  I
241  CCGCCTTAGC TGCACCTACG GCAGCGTTGA TAGCGCGGAT TTATGAGCGA GCACACCATC
     GGCGGAATCG ACGTGGATGC CGTCGCAACT ATCGCGCCTA AATACTCGCT CGTGTGGTAG +1  A  H  S  I    T  L  P    P  G  Y    T  L  A  L    I  P  P    E  P  E
301  GCCCACTCCA TCACATTACC ACCCGGTTAC ACCCTTGCCC TAATACCCCC TGAACCTGAA
     CGGGTGAGGT AGTGTAATGG TGGGCCAATG TGGGAACGGG ATTATGGGGG ACTTGGACTT
        p71 start (SEQ ID NO:3)
 +3     M  G  D  A  G    V  A  S  Q    R  P  H    N  R  R    G  T  R
 +1  A  G  W  E    M  L  E    W  R  H    S  D  L  T    T  V  A    E  P  V
361  GCAGGATGGG AGATGCTGGA GTGGCGTCAC AGCGACCTCA CAACCGTCGC GGAACCCGTA
     CGTCCTACCC TCTACGACCT CACCGCAGTG TCGCTGGAGT GTTGGCAGCG CCTTGGGCAT +3  N  V  R  V    S  A  N    T  V  T  V    N  G  R    R  N  Q    R  R  R
 +1  T  F  G  S    A  P  T    P  S  P    S  M  V  E    E  T  N    G  V  G
421  ACGTTCGGGT CAGCGCCAAC ACCGTCACCG TCAATGGTAG AAGAAACCAA CGGCGTCGGA
     TGCAAGCCCA GTCGCGGTTG TGGCAGTGGC AGTTACCATC TTCTTTGGTT GCCGCAGCCT +3  T  G  R  Q    V  S  P    P  D  N  F    T  A  A    A  Q  D    L  A  Q
 +1  P  E  G  K    F  L  P    L  T  I    S  P  L  L    H  K  T    S  R  K
481  CCGGAAGGCA AGTTTCTCCC CCTGACAATT TCACCGCTGC TGCACAAGAC CTCGCGCAAA
     GGCCTTCCGT TCAAAGAGGG GGACTGTTAA AGTGGCGACG ACGTGTTCTG GAGCGCGTTT +3  S  L  D  A    N  T  V    T  F  P  A    N  I  S    S  M  P    E  F  R
 +1  A  L  T  P    T  P  S    L  S  P    L  T  S  L    A  C  P    N  S  G
541  GCCTTGACGC CAACACCGTC ACTTTCCCCG CTAACATCTC TAGCATGCCC GAATTCCGGA
     CGGAACTGCG GTTGTGGCAG TGAAAGGGGC GATTGTAGAG ATCGTACGGG CTTAAGGCCT +3  N  W  A  K    G  K  I    D  L  D  S    D  S  I    G  W  Y    F  K  Y
 +1  I  G  P  R    E  R  S    T  S  T    P  I  P  S    A  G  T    S  S  T
601  ATTGGGCCAA GGGAAAGATC GACCTCGACT CCGATTCCAT CGGCTGGTAC TTCAAGTACC
     TAACCCGGTT CCCTTTCTAG CTGGAGCTGA GGCTAAGGTA GCCGACCATG AAGTTCATGG +3  L  D  P  A    G  A  T    E  S  A  R    A  V  G    E  Y  S    K  I  P
 +1  L  T  Q  R    V  L  Q    S  L  R    A  P  S  A    S  T  R    R  S  L
661  TTGACCCAGC GGGTGCTACA GAGTCTGCGC GCGCCGTCGG CGAGTACTCG AAGATCCCTG
     AACTGGGTCG CCCACGATGT CTCAGACGCG CGCGGCAGCC GCTCATGAGC TTCTAGGGAC
```

Figure 1

```
        (SEQ ID NO:1)
  1     GTTTTTCTTT CTTTACCAAG TGTGGTAAAA TTTAAACAAA GAAGAAAACC AGGACCGTAA
        CAAAAAGAAA GAAATGGTTC ACACCATTTT AAATTTGTTT CTTCTTTTGG TCCTGGCATT

61     CCCGGCCCTT ACACACCTCG AGTCCGTGAC CACCGGATTA TACGTCGCCC ACCACACGGC
        GGGCCGGGAA TGTGTGGAGC TCAGGCACTG GTGGCCTAAT ATGCAGCGGG TGGTGTGCCG

121     GCCTTTTCCG ACCACTCTCG AGAGTCGTTG GGAGTTTCGT CCGTGACCAC CCGGTTGGCA
        CGGAAAAGGC TGGTGAGAGC TCTCAGCAAC CCTCAAAGCA GGCACTGGTG GGCCAACCGT

81     GTCGACAGAC GCTTCCGGAC CACTAGAACC TCCTCGAGCG ACGCACACAC AGCACACACA
        CAGCTGTCTG CGAAGGCCTG GTGATCTTGG AGGAGCTCGC TGCGTGTGTG TCGTGTGTGT
                                                                 p17 start
 +1                                                   (SEQ ID NO:2)M  S    E    H    T    I
241     CCGCCTTAGC TGCACCTACG GCAGCGTTGA TAGCGCGGAT TTATGAGCGA GCACACCATC
        GGCGGAATCG ACGTGGATGC CGTCGCAACT ATCGCGCCTA AATACTCGCT CGTGTGGTAG +1  A    H    S    I    T    L    P    G    Y    T    L    A    L    I    P    P    E    P    E
301     GCCCACTCCA TCACATTACC ACCCGGTTAC ACCCTTGCCC TAATACCCCC TGAACCTGAA
        CGGGTGAGGT AGTGTAATGG TGGGCCAATG TGGGAACGGG ATTATGGGGG ACTTGGACTT
                p71 start (SEQ ID NO:3)
 +3          M    G    D    A    G    V    A    S    Q    R    P    H    N    R    R    G    T    R
 +1  A    G    W    E    M    L    E    W    R    H    S    D    L    T    T    V    A    E    P    V
361     GCAGGATGGG AGATGCTGGA GTGGCGTCAC AGCGACCTCA CAACCGTCGC GGAACCCGTA
        CGTCCTACCC TCTACGACCT CACCGCAGTG TCGCTGGAGT GTTGGCAGCG CCTTGGGCAT +3  N    V    R    V    S    A    N    T    V    T    V    N    G    R    N    Q    R    R    R
 +1  T    F    G    S    A    P    T    P    S    P    S    M    V    E    E    T    N    G    V    G
421     ACGTTCGGGT CAGCGCCAAC ACCGTCACCG TCAATGGTAG AAGAAACCAA CGGCGTCGGA
        TGCAAGCCCA GTCGCGGTTG TGGCAGTGGC AGTTACCATC TTCTTTGGTT GCCGCAGCCT +3  T    G    R    Q    V    S    P    P    D    N    F    T    A    A    Q    D    L    A    Q
 +1  P    E    G    K    F    L    P    L    T    I    S    P    L    L    H    K    T    S    R    K
481     CCGGAAGGCA AGTTTCTCCC CCTGACAATT TCACCGCTGC TGCACAAGAC TCGCGCAAA
        GGCCTTCCGT TCAAAGAGGG GGACTGTTAA AGTGGCGACG ACGTGTTCTG AGCGCGTTT +3  S    L    D    A    N    T    V    T    F    P    A    N    I    S    S    M    P    E    F    R
 +1  A    L    T    P    T    P    S    L    S    P    L    T    S    L    A    C    P    N    S    G
541     GCCTTGACGC CAACACCGTC ACTTTCCCCG CTAACATCTC TAGCATGCCC GAATTCCGGA
        CGGAACTGCG GTTGTGGCAG TGAAAGGGGC GATTGTAGAG ATCGTACGGG CTTAAGGCCT +3  N    W    A    K    G    K    I    D    L    D    S    D    S    I    G    W    Y    F    K    Y
 +1  I    G    P    R    E    R    S    T    S    T    P    I    P    S    A    G    T    S    S    T
601     ATTGGGCCAA GGGAAAGATC GACCTCGACT CCGATTCCAT CGGCTGGTAC TTCAAGTACC
        TAACCCGGTT CCCTTTCTAG CTGGAGCTGA GGCTAAGGTA GCCGACCATG AAGTTCATGG +3  L    D    P    A    G    A    T    E    S    A    R    A    V    G    E    Y    S    K    I    P
 +1  L    T    Q    R    V    L    Q    S    L    R    A    P    S    A    S    T    R    R    S    L
661     TTGACCCAGC GGGTGCTACA GAGTCTGCGC GCGCCGTCGG CGAGTACTCG AAGATCCCTG
        AACTGGGTCG CCCACGATGT CTCAGACGCG CGCGGCAGCC GCTCATGAGC TTCTAGGGAC
```

Fig. 1 cont.

```
     +3  D   G   L   V   K   F   S   V   D   A   E   I   R   E   I   Y   N   E   E   C
     +1  T   A   S   S   S   S   P   S   T   Q   R   *
     721 ACGGCCTCGT CAAGTTCTCC GTCGACGCAG AGATAAGAGA GATCTATAAC GAGGAGTGCC
         TGCCGGAGCA GTTCAAGAGG CAGCTGCGTC TCTATTCTCT CTAGATATTG CTCCTCACGG

+3  P   V   V   T   D   V   S   V   P   L   D   G   R   Q   W   S   L   S   I   F
     781 CCGTCGTCAC TGACGTGTCC GTCCCCCTCG ACGGCCGCCA GTGGAGCCTC TCGATTTTCT
         GGCAGCAGTG ACTGCACAGG CAGGGGGAGC TGCCGGCGGT CACCTCGGAG AGCTAAAAGA

+3  S   F   P   M   F   R   T   A   Y   V   A   V   A   N   V   E   N   K   E   M
     841 CCTTTCCGAT GTTCAGAACC GCCTACGTCG CCGTAGCGAA CGTCGAGAAC AAGGAGATGT
         GGAAAGGCTA CAAGTCTTGG CGGATGCAGC GGCATCGCTT GCAGCTCTTG TTCCTCTACA

+3  S   L   D   V   V   N   D   L   I   E   W   L   N   N   L   A   D   W   R   Y
     901 CGCTCGACGT TGTCAACGAC CTCATCGAGT GGCTCAACAA TCTCGCCGAC TGGCGTTATG
         GCGAGCTGCA ACAGTTGCTG GAGTAGCTCA CCGAGTTGTT AGAGCGGCTG ACCGCAATAC

+3  V   V   D   S   E   Q   W   I   N   F   T   N   D   T   T   Y   Y   V   R   I
     961 TCGTTGACTC TGAACAGTGG ATTAACTTCA CCAATGACAC CACGTACTAC GTCCGCATCC
         AGCAACTGAG ACTTGTCACC TAATTGAAGT GGTTACTGTG GTGCATGATG CAGGCGTAGG

+3  R   V   L   R   P   T   Y   D   V   P   D   P   T   E   G   L   V   R   T   V
    1021 GCGTTCTACG TCCAACCTAC GACGTTCCAG ACCCCACAGA GGGCCTTGTT CGCACAGTCT
         CGCAAGATGC AGGTTGGATG CTGCAAGGTC TGGGGTGTCT CCCGGAACAA GCGTGTCAGA

+3  S   D   Y   R   L   T   Y   K   A   I   T   C   E   A   N   M   P   T   L   V
    1081 CAGACTACCG CCTCACTTAT AAGGCGATAA CATGTGAAGC CAACATGCCA ACACTCGTCG
         GTCTGATGGC GGAGTGAATA TTCCGCTATT GTACACTTCG GTTGTACGGT TGTGAGCAGC

+3  D   Q   G   F   W   I   G   G   Q   Y   A   L   T   P   T   S   L   P   Q   Y
    1141 ACCAAGGCTT TTGGATCGGC GGCCAGTACG CTCTCACCCC GACTAGCCTA CCGCAGTACG
         TGGTTCCGAA AACCTAGCCG CCGGTCATGC GAGAGTGGGG CTGATCGGAT GGCGTCATGC

+3  D   V   S   E   A   Y   A   L   H   T   L   T   F   A   R   P   S   A   A
    1201 ACGTCAGCGA GGCCTACGCT CTGCACACTT TGACCTTCGC CAGACCATCC AGCGCCGCTG
         TGCAGTCGCT CCGGATGCGA GACGTGTGAA ACTGGAAGCG GTCTGGTAGG TCGCGGCGAC

+3  A   L   A   F   V   W   A   G   L   P   Q   G   G   T   A   P   A   G   T   P
    1261 CACTCGCGTT TGTGTGGGCA GGTTTGCCAC AGGGTGGCAC TGCGCCTGCA GGCACTCCAG
         GTGAGCGCAA ACACACCCGT CCAAACGGTG TCCCACCGTG ACGCGGACGT CCGTGAGGTC

+3  A   W   E   Q   A   S   S   G   G   Y   L   T   W   R   H   N   G   T   T   F
    1321 CCTGGGAGCA GGCATCCTCG GGTGGCTACC TCACCTGGCG CCACAACGGT ACTACTTTCC
         GGACCCTCGT CCGTAGGAGC CCACCGATGG AGTGGACCGC GGTGTTGCCA TGATGAAAGG

+3  P   A   G   S   V   S   Y   V   L   P   E   G   F   A   L   E   R   Y   D   P
    1381 CAGCTGGCTC CGTTAGCTAC GTTCTCCCTG AGGGTTTCGC CCTTGAGCGC TACGACCCGA
         GTCGACCGAG GCAATCGATG CAAGAGGGAC TCCCAAAGCG GGAACTCGCG ATGCTGGGCT
```

Fig. 1 cont.

```
      +3  N   D   G   S       W   T   D       F   A   S   A       G   D   T       V   T   F       R   Q   V
    1441  ACGACGGCTC  TTGGACCGAC  TTCGCTTCCG  CAGGAGACAC  CGTCACTTTC  CGGCAGGTCG
          TGCTGCCGAG  AACCTGGCTG  AAGCGAAGGC  GTCCTCTGTG  GCAGTGAAAG  GCCGTCCAGC

+3  A   V   D   E       V   V   V       T   N   N   P       A   G   G       G   S   A       P   T   F
    1501  CCGTCGACGA  GGTCGTTGTG  ACCAACAACC  CCGCCGGCGG  CGGCAGCGCC  CCCACCTTCA
          GGCAGCTGCT  CCAGCAACAC  TGGTTGTTGG  GGCGGCCGCC  GCCGTCGCGG  GGGTGGAAGT

+3  T   V   R   V       P   P   S       N   A   Y   T       N   T   V       F   R   N       T   L   L
    1561  CCGTGAGAGT  GCCCCCTTCA  AACGCTTACA  CCAACACCGT  GTTTAGGAAC  ACGCTCTTAG
          GGCACTCTCA  CGGGGGAAGT  TTGCGAATGT  GGTTGTGGCA  CAAATCCTTG  TGCGAGAATC

+3  E   T   R   P       S   S   R       R   L   E   L       P   M   P       P   A   D       F   G   Q
    1621  AGACTCGACC  CTCCTCTCGT  AGGCTCGAAC  TCCCTATGCC  ACCTGCTGAC  TTTGGACAGA
          TCTGAGCTGG  GAGGAGAGCA  TCCGAGCTTG  AGGGATACGG  TGGACGACTG  AAACCTGTCT

+3  T   V   A   N       P   K       I   E   Q   S       L   L   K       E   T   L       G   C   Y
    1681  CGGTCGCCAA  CAACCCGAAG  ATCGAGCAGT  CGCTTCTTAA  AGAAACACTT  GGCTGCTATT
          GCCAGCGGTT  GTTGGGCTTC  TAGCTCGTCA  GCGAAGAATT  TCTTTGTGAA  CCGACGATAA

+3  L   V   H   S       K   M   R       N   P   V   F       Q   L   T       P   A   S       S   F   G
    1741  TGGTCCACTC  CAAAATGCGA  AACCCCGTTT  CCAGCTCAC   GCCAGCCAGC  TCCTTTGGCG
          ACCAGGTGAG  GTTTTACGCT  TTGGGGCAAA  AGGTCGAGTG  CGGTCGGTCG  AGGAAACCGC

+3  A   V   S   F       N   N   P       G   Y   E   R       T   R   D       L   P   D       Y   T   G
    1801  CCGTTTCCTT  CAACAATCCG  GGTTATGAGC  GCACACGCGA  CCTCCCGGAC  TACACTGGCA
          GGCAAAGGAA  GTTGTTAGGC  CCAATACTCG  CGTGTGCGCT  GGAGGGCCTG  ATGTGACCGT

+3  I   R   D   S       F   D   Q       N   M   S   T       A   V   A       H   F   R       S   L   S
    1861  TCCGTGACTC  ATTCGACCAG  AACATGTCCA  CCGCTGTGGC  CCACTTCCGC  TCACTCTCCC
          AGGCACTGAG  TAAGCTGGTC  TTGTACAGGT  GGCGACACCG  GGTGAAGGCG  AGTGAGAGGG

+3  H   S   C   S       I   V   T       K   T   Y   Q       G   W   E       G   V   T       N   V   N
    1921  ACTCCTGCAG  TATCGTCACT  AAGACCTACC  AGGGTTGGGA  AGGCGTCACG  AACGTCAACA
          TGAGGACGTC  ATAGCAGTGA  TTCTGGATGG  TCCCAACCCT  TCCGCAGTGC  TTGCAGTTGT

+3  T   P   F   G       Q   F   A       H   A   G   L       L   K   N       E   E   I       L   C   L
    1981  CGCCTTTCGG  CCAATTCGCG  CACGCGGGCC  TCCTCAAGAA  TGAGGAGATC  CTCTGCCTCG
          GCGGAAAGCC  GGTTAAGCGC  GTGCGCCCGG  AGGAGTTCTT  ACTCCTCTAG  GAGACGGAGC

+3  A   D   D   L       A   T   R       L   T   G   V       Y   P   A       T   D   N       F   A   A
    2041  CCGACGACCT  GGCCACCCGT  CTCACAGGTG  TCTACCCCGC  CACTGACAAC  TTCGCGGCCG
          GGCTGCTGGA  CCGGTGGGCA  GAGTGTCCAC  AGATGGGGCG  GTGACTGTTG  AAGCGCCGGC

+3  A   V   S   A       F   A   A       N   M   L   S       S   V   L       K   S   E       A   T   S
    2101  CCGTTTCTGC  CTTCGCCGCG  AACATGCTGT  CCTCCGTGCT  GAAGTCGGAG  GCAACGTCCT
          GGCAAAGACG  GAAGCGGCGC  TTGTACGACA  GGAGGCACGA  CTTCAGCCTC  CGTTGCAGGA
```

Fig. 1 cont.

```
     +3  S   I   I   K     S   V   G     E   T   A   V     G   A   A     Q   S   G     L   A   K
    2161  CCATCATCAA GTCCGTTGGC GAGACTGCCG TCGGCGCGGC TCAGTCCGGC CTCGCGAAGC
          GGTAGTAGTT CAGGCAACCG CTCTGACGGC AGCCGCGCCG AGTCAGGCCG GAGCGCTTCG

+3  L   P   G   L     M   S     V   P   G   K     I   A   A     R   V   R     A   R   R
    2221  TACCCGGACT GCTAATGAGT GTACCAGGGA AGATTGCCGC GCGTGTCCGC GCGCGCCGAG
          ATGGGCCTGA CGATTACTCA CATGGTCCCT TCTAACGGCG CGCACAGGCG CGCGCGGCTC

+3  A   R   R   R     A   A   R     A   N   *
    2281  CGCGCCGCCG CGCCGCTCGT GCCAATTAGT TTGCTCGCTC CTGTTTCGCC GTTTCGTAAA
          GCGCGGCGGC GCGGCGAGCA CGGTTAATCA AACGAGCGAG GACAAAGCGG CAAAGCATTT

2341  ACGGCGTGGT CCCGCACATT ACGCGTACCC TAAAGACTCT GGTGAGTCCC CGTCGTTACA
          TGCCGCACCA GGGCGTGTAA TGCGCATGGG ATTTCTGAGA CCACTCAGGG GCAGCAATGT

2401  CGACGGGTCT GCCGCGGTTC GATTCCATTC CCAAGCGGCA AGAAGGACGT AGTTAGCTCT
          GCTGCCCAGA CGGCGCCAAG CTAAGGTAAG GGTTCGCCGT TCTTCCTGCA TCAATCGAGA

2461  GCGTCCCTCG GGATACCA
          CGCAGGGAGC CCTATGGT
```

Figure 2

```
       (SEQ ID NO:4)
   +1                       (SEQ ID NO:5)    M   E   D   A   S   K   Q       L   R   V
    1  CCTTGATATC GCTTGTGTTA GGCACAAGTG ATGGAAGACG CAAGCAAGCA GCTCCGCGTC
       GGAACTATAG CGAACACAAT CCGTGTTCAC TACCTTCTGC GTTCGTTCGT CGAGGCGCAG

+1  L   D   A   Q       E   R   A   K   A   A       F   Q   L   D       F   I   A   S   V   E
   61  CTGGATGCCC AGGAGCGCGC GAAGGCCGCC TTCCAACTCG ACTTCATAGC CTCTGTCGAG
       GACCTACGGG TCCTCGCGCG CTTCCGGCGG AAGGTTGAGC TGAAGTATCG GAGACAGCTC

+1  T   L   E   D       A   Q       E   K   Y   E       G   M   M       F   R   S       G       T   K   L
  121  ACTTTGGAAG ACGCTCAGGA GAAGTACGAG GGCATGATGT TCGCAGTGG CACGAAACTG
       TGAAACCTTC TGCGAGTCCT CTTCATGCTC CCGTACTACA AGCGTCACC GTGCTTTGAC

+1  P   S   T   H       I   K   L       A   I   D       L   R   V   A   E   K   D       L   R   R
  181  CCATCAACCC ATATTAAGTT GGCAATCGAT CTGAGAGTTG CGGAGAAAGA TCTACGCCGG
       GGTAGTTGGG TATAATTCAA CCGTTAGCTA GACTCTCAAC GCCTCTTTCT AGATGCGGCC

+1  H   V   K   N   V   P   T       V   L   E       I   G   P   S       V   E   S       V   R   Y
  241  CACGTTAAGA ATGTACCGAC AGTGCTGGAA ATTGGACCCA GTGTTGAGAG CGTGCGTTAC
       GTGCAATTCT TACATGGCTG TCACGACCTT TAACCTGGGT CACAACTCTC GCACGCAATG

+1  A   V   Q   T       R   D   K       E   R   V       H   G   C       T       F   S   D       A   R   D
  301  GCTGTGCAGA CTCGAGACAA GGAGAGAGTC CATGGCTGCA CCTTCTCCGA CGCGCGTGAT
       CGACACGTCT GAGCTCTGTT CCTCTCTCAG GTACCGACGT GGAAGAGGCT GCGCGCACTA

+1  N   L   R   H   N   K   I       G   Y   E       A   H   Y   D   R   K   I       G   P   D
  361  AACCTCCGCC ACAATAAGAT CGGTTATGAA GCCCATTACG ACAGAAAGAT TGGACCTGAC
       TTGGAGGCGG TGTTATTCTA GCCAATACTT CGGGTAATGC TGTCTTTCTA ACCTGGACTG

+1  A   A   L   L       A   A   G       I   P   T       D   T   F       C   V   D   G       F   S   N
  421  GCCGCCCTTC TGGCCGCTGG TATCCCAACT GACACCTTCT GTGTCGACGG CTTCTCCAAT
       CGGCGGGAAG ACCGGCGACC ATAGGGTTGA CTGTGGAAGA CACAGCTGCC GAAGAGGTTA

+1  C   E   Y   Q   S   P   L       A   I   A       C   H   S   L       Y   P   D       G   E   S
  481  TGCGAGTACC AATCCCCCCT CGCCATTGCC TGCCACTCAC TTTACCCCGA TGGGGAAAGT
       ACGCTCATGG TTAGGGGGA GCGGTAACGG ACGGTGAGTG AAATGGGGCT ACCCCTTTCA

+1  N   S   I   M       D   V   A       K   G   M       A   L   H   G       T   H   V       I   Y   A
  541  AATAGTATTA TGGACGTGGC TAAAGGCATG GCTCTCCACG GCACCCACGT GATATATGCG
       TTATCATAAT ACCTGCACCG ATTTCCGTAC CGAGAGGTGC CGTGGGTGCA CTATATACGC

+1  W   M   H   L       P   V   E       L   L   T       L   T   D   A   D   N   I       F   E   G
  601  TGGATGCATC TGCCCGTGGA ACTGCTAACG CTCACCGATG CAGACAATAT TTTTGAAGGG
       ACCTACGTAG ACGGGCACCT TGACGATTGC GAGTGGCTAC GTCTGTTATA AAAACTTCCC

+1  Y   S   I   R       F   E   E       T   G   A       L   P   C   T       K   R   R       K   A   I
  661  TATAGCATTC GGTTTGAGGA GACAGGGGCA CTACCCTGCA CCAAGAGGAG GAAAGCCATA
       ATATCGTAAG CCAAACTCCT CTGTCCCCGT GATGGGACGT GGTTCTCCTC CTTTCGGTAT
```

Fig. 2 cont.

```
      +1   F    S    G    Y    N    D    F    G    S    A    Y    V    H    D    A    H    H    W    A    G
     721   TTCTCCGGTT ATAACGATTT TGGTTCGGCC TATGTGCACG ATGCCCACCA TTGGGCTGGT
           AAGAGGCCAA TATTGCTAAA ACCAAGCCGG ATACACGTGC TACGGGTGGT AACCCGACCA

+1   W    L    K    H    R    G    V    D    T    P    Y    G    F    S    I    L    I    D    I    Q
     781   TGGCTTAAGC ATCGGGGAGT AGACACCCCG TATGGCTTCT CCATATTGAT CGACATACAA
           ACCGAATTCG TAGCCCCTCA TCTGTGGGGC ATACCGAAGA GGTATAACTA GCTGTATGTT

+1   Q    R    F    G    M    H    T    K    L    K    I    T    R    G    H    S    S    G    S    I
     841   CAGAGGTTCG GTATGCACAC GAAATTAAAG ATCACCCGTG GGCACAGCAG TGGCAGTATC
           GTCTCCAAGC CATACGTGTG CTTTAATTTC TAGTGGGCAC CCGTGTCGTC ACCGTCATAG

+1   T    T    V    F    P    L    S    K    L    G    L    I    W    V    P    N    I    V    K    I
     901   ACCACCGTGT TCCCGTTGTC GAAATTGGGC TTGATCTGGG TGCCGAACAT AGTCAAAATA
           TGGTGGCACA AGGGCAACAG CTTTAACCCG AACTAGACCC ACGGCTTGTA TCAGTTTTAT

+1   M    Y    P    K    A    K    H    E    P    E    Y    I    V    T    D    K    K    K    Y    E
     961   ATGTACCCTA AAGCCAAACA CGAGCCGGAG TACATCGTCA CGGATAAGAA GAAGTATGAA
           TACATGGGAT TTCGGTTTGT GCTCGGCCTC ATGTAGCAGT GCCTATTCTT CTTCATACTT

+1   G    V    C    V    Y    V    G    T    R    V    Q    S    S    G    K    S    I    T    L    A
    1021   GGCGTTTGCG TGTACGTCGG AACGAGGGTG CAAAGTTCCG GCAAGTCTAT TACGCTCGCT
           CCGCAAACGC ACATGCAGCC TTGCTCCCAC GTTTCAAGGC CGTTCAGATA ATGCGAGCGA

+1   E    I    V    Q    Y    I    R    T    R    L    T    R    I    I    L    N    G    T    V    H
    1081   GAGATTGTTC AATACATCCG AACAAGATTA ACACGCATCA TTCTGAATGG CACTGTCCAC
           CTCTAACAAG TTATGTAGGC TTGTTCTAAT TGTGCGTAGT AAGACTTACC GTGACAGGTG

+1   E    K    T    W    T    I    A    E    Q    D    I    E    R    L    A    V    S    I    M    F
    1141   GAGAAAACGT GGACCATAGC AGAGCAAGAC ATTGAGCGAC TTGCCGTTAG CATTATGTTC
           CTCTTTTGCA CCTGGTATCG TCTCGTTCTG TAACTCGCTG AACGGCAATC GTAATACAAG

+1   R    K    N    V    E    R    A    V    S    E    K    A    L    M    R    A    Q    K    K    C
    1201   CGCAAGAATG TGGAACGCGC TGTGTCTGAA AAGGCACTGA TGAGAGCGCA AAAGAAGTGC
           GCGTTCTTAC ACCTTGCGCG ACACAGACTT TTCCGTGACT ACTCTCGCGT CTTCTTCACG

+1   K    S    A    E    K    Q    A    L    L    P    V    W    M    R    R    I    A    N    W    F
    1261   AAGAGCGCTG AAAAACAAGC GCTGCTGCCA GTTTGGATGC GGAGGATCGC CAATTGGTTC
           TTCTCGCGAC TTTTTGTTCG CGACGACGGT CAAACCTACG CCTCCTAGCG GTTAACCAAG

+1   Q    D    K    F    Q    I    D    E    E    V    R    K    R    Y    L    E    C    L    K
    1321   CAAGACAAAT TTCAAATCGA CGAGGAGGTC GTACGCAAGC GCTACCTTGA GTGTCTCAAG
           GTTCTGTTTA AAGTTTAGCT GCTCCTCCAG CATGCGTTCG CGATGGAACT CACAGAGTTC

+1   A    Q    P    W    I    H    A    D    K    V    V    N    C    E    T    K    R    Y    N    P
    1381   GCGCAACCCT GGATCCACGC CGATAAAGTG GTGAACTGCG AGACCAAGCG CTATAACCCT
           CGCGTTGGGA CCTAGGTGCG GCTATTTCAC CACTTGACGC TCTGGTTCGC GATATTGGGA
```

Fig. 2 cont.

```
      +1    T   V   A   E       V   G   P       K   N   H       L   L   A       T   G   L       R   E   L
    1441    ACTGTCGCCG  AGGTGGGTCC  TAAGAATCAT  TTGCTCGCCA  CTACCGGATT  GCGCGAGCTC
            TGACAGCGGC  TCCACCCAGG  ATTCTTAGTA  AACGAGCGGT  GATGGCCTAA  CGCGCTCGAG

+1    Q   R   E       I   P   S       N   E   P       Q   D   R       G   A   K       A   W   H   S
    1501    CAAAGGGAAA  TACCCAGTGC  TAACGAACCG  CAAGATAGAG  GAGCCAAGGC  ATGGCACTCC
            GTTTCCCTTT  ATGGGTCACG  ATTGCTTGGC  GTTCTATCTC  CTCGGTTCCG  TACCGTGAGG

+1    A   H   A   D       L   D   I       Y   A   E       G   L   R       L   D   S       A   K   E   A
    1561    GCTCACGCCG  ATCTCGACAT  TTACGCCGAG  GGACTCCGAC  TCGACTCCGC  TAAAGAGGCA
            CGAGTGCGGC  TAGAGCTGTA  AATGCGGCTC  CCTGAGGCTG  AGCTGAGGCG  ATTTCTCCGT

+1    A   A   G   K       Q   S   L       A   I   T       L   Q   Q   A       F   Q   V       L   G   K
    1621    GCAGCGGGTA  AGCAGTCCCT  GGCGATCACA  TTGCAGCAAG  CTTTCCAAGT  CCTAGGGAAG
            CGTCGCCCAT  TCGTCAGGGA  CCGCTAGTGT  AACGTCGTTC  GAAAGGTTCA  GGATCCCTTC

+1    T   K   C   E       G   C   N       N   I   E       I   E   Y   W       T   G   P       P   G   S
    1681    ACCAAGTGCG  AGGGGTGCAA  CAACATTGAA  ATCGAGTACT  GGACCGGACC  CCCCGGTTCC
            TGGTTCACGC  TCCCCACGTT  GTTGTAACTT  TAGCTCATGA  CCTGGCCTGG  GGGGCCAAGG

+1    G   K   S       R   A   A   K       P   R   F       A   D   L   Q       G   G   V       L   Y   C
    1741    GGGAAATCCA  GGGCCGCTAA  GCCGAGATTT  GCAGATTTGC  AGGGGGGCGT  GTTGTACTGC
            CCCTTTAGGT  CCCGGCGATT  CGGCTCTAAA  CGTCTAAACG  TCCCCCCGCA  CAACATGACG

+1    A   P   T   R       T   L   R       D   A   L       D   E   S   V       H   P       S   R   V
    1801    GCCCCTACGC  GCACGCTGCG  CGACGCCCTC  GACGAAAGCG  TCGTGCACCC  TTCCCGTGTT
            CGGGGATGCG  CGTGCGACGC  GCTGCGGGAG  CTGCTTTCGC  AGCACGTGGG  AAGGGCACAA

+1    C   T   Y       H   N   A   L       H   V   A       A   K   E   S       G   N   R       P   F   D
    1861    TGCACTTACC  ACAACGCACT  GCATGTCGCT  GCCAAAGAGT  CTGGCAATAG  GCCTTTTGAC
            ACGTGAATGG  TGTTGCGTGA  CGTACAGCGA  CGGTTTCTCA  GACCGTTATC  CGGAAAACTG

+1    V   I   V   I       D   E   A       E   T   T       P   A   C   Y       V   G   T       M   H   H
    1921    GTTATCGTCA  TCGATGAAGC  GGAGACGACG  CCGGCTTGCT  ACGTAGGTAC  GATGCATCAT
            CAATAGCAGT  AGCTACTTCG  CCTCTGCTGC  GGCCGAACGA  TGCATCCATG  CTACGTAGTA

+1    A   S   P   S       S   R   I       V   C   L       G   D   P   H       Q   I   G       Y   I   D
    1981    GCATCGCCTA  GTAGTAGGAT  CGTCTGTCTG  GGCGATCCGC  ACCAGATCGG  TTACATCGAC
            CGTAGCGGAT  CATCATCCTA  GCAGACAGAC  CCGCTAGGCG  TGGTCTAGCC  AATGTAGCTG

+1    F   S   D   R       K   D   D       L   K   P       F   S   I   I       A   A   E       C   R   T
    2041    TTTTCGGATC  GAAAAGACGA  TTTGAAACCT  TTCAGTATCA  TAGCAGCCGA  ATGTCGCACT
            AAAAGCCTAG  CTTTTCTGCT  AAACTTTGGA  AAGTCATAGT  ATCGTCGGCT  TACAGCGTGA

+1    R   R   F   N       T   T   Y       R   C   P       Q   D   V   L       N   L   P       I   F   K
    2101    CGTAGGTTTA  ACACCACTTA  TAGGTGCCCA  CAAGACGTTT  TAAACTTGCC  CATATTCAAA
            GCATCCAAAT  TGTGGTGAAT  ATCCACGGGT  GTTCTGCAAA  ATTTGAACGG  GTATAAGTTT
```

Fig. 2 cont.

```
      +1    T   L   Y   P   D   A   I     S   F   S   K   Q   L   T     S   I   R   Y   L   T
    2161    ACTCTATACC  CGGACGCGAT  ATCGTTCAGC  AAACAATTGA  CTAGCATCCG  TTACCTCACA
            TGAGATATGG  GCCTGCGCTA  TAGCAAGTCG  TTTGTTAACT  GATCGTAGGC  AATGGAGTGT

+1    R   A   R   S   V   T   R     T   R   H   A   Q   T   L     T   Q   D   Q   K   P
    2221    CGGGCAAGAT  CAGTTACCCG  AACACGCCAC  GCTCAGACCC  TGACGCAGGA  CCAAAAGCCA
            GCCCGTTCTA  GTCAATGGGC  TTGTGCGGTG  CGAGTCTGGG  ACTGCGTCCT  GGTTTTCGGT

+1    H   S   E   P   P   V   T     A   H   E   P   Q   A   R     R   T   D   V   I   V
    2281    CATTCGGAAC  CGCCAGTGAC  CGCGCATGAG  CCGCAGGCAC  GACGTACGGA  CGTTATAGTG
            GTAAGCCTTG  GCGGTCACTG  GCGCGTACTC  GGCGTCCGTG  CTGCATGCCT  GCAATATCAC

+1    H   Y   A   G   T   L   P     E   R   A   L   L   E   K     V   R   H   I   N   V
    2341    CATTACGCCG  GCACTTTACC  CGAAAGGGCA  CTGTTAGAGA  AGGTGCGGCA  TATAAACGTC
            GTAATGCGGC  CGTGAAATGG  GCTTTCCCGT  GACAATCTCT  TCCACGCCGT  ATATTTGCAG

+1    A   L   T   R   H   T   N     A   L   Y   I   R   D   E     S   E   K   G   E   L
    2401    GCGTTGACTC  GGCACACAAA  CGCCCTATAT  ATCAGGGACG  AAAGTGAAAA  AGGAGAGTTG
            CGCAACTGAG  CCGTGTGTTT  GCGGGATATA  TAGTCCCTGC  TTTCACTTTT  TCCTCTCAAC

+1    V   P   S   L   M   T   P     P   S   W   S   T   Y   R     C   T   P   V   D   K
    2461    GTACCTTCAT  TAATGACACC  GCCAAGCTGG  AGCACTTATC  GGTGCACCCC  CGTTGACAAG
            CATGGAAGTA  ATTACTGTGG  CGGTTCGACC  TCGTGAATAG  CCACGTGGGG  GCAACTGTTC

+1    Q   M   V   P   D   P   V     A   V   E   R   E   N   G     S   S   G   P   C   D
    2521    CAAATGGTAC  CGGATCCGGT  TGCAGTGGAG  CGAGAGAACG  GATCGTCTGG  TCCGTGTGAC
            GTTTACCATG  GCCTAGGCCA  ACGTCACCTC  GCTCTCTTGC  CTAGCAGACC  AGGCACACTG

+1    S   H   H   I   G   A   I     T   I   L   Q   E   L   G     K   L   T   D   T   K
    2581    TCCCACCATA  TCGGCGCGAT  TACTATATTG  CAAGAGCTCG  GCAAATTAAC  GGATACGAAA
            AGGGTGGTAT  AGCCGCGCTA  ATGATATAAC  GTTCTCGAGC  CGTTTAATTG  CCTATGCTTT

+1    G   V   R   V   F   E   S     E   A   V   P   T   A   H     R   R   V   V   L   D
    2641    GGCGTACGAG  TATTTGAATC  CGAAGCCGTC  CCAACCGCTC  ACCGGCGCGT  AGTGCTTGAC
            CCGCATGCTC  ATAAACTTAG  GCTTCGGCAG  GGTTGGCGAG  TGGCCGCGCA  TCACGAACTG

+1    G   N   L   D   S   G   P     D   R   Y   P   M   Y   Q     F   T   N   L   R   G
    2701    GGCAACCTCG  ATTCAGGGCC  CGATCGTTAC  CCGATGTATC  AGTTCACTAA  CCTCCGCGGG
            CCGTTGGAGC  TAAGTCCCGG  GCTAGCAATG  GGCTACATAG  TCAAGTGATT  GGAGGCGCCC

+1    T   K   Y   T   N   I   K     D   N   Q   Q   A   L   H     T   L   V   G   R   Y
    2761    ACCAAATACA  CGAATATCAA  GGACAACCAA  CAAGCGTTGC  ATACGCTCGT  CGGCCGGTAT
            TGGTTTATGT  GCTTATAGTT  CCTGTTGGTT  GTTCGCAACG  TATGCGAGCA  GCCGGCCATA

+1    A   R   K   I   N   S   S     S   R   E   T   P   S   L     T   L   R   E   S   Q
    2821    GCACGCAAGA  TAAACAGCTC  GAGCCGAGAG  ACGCCGAGTT  TGACGTTAAG  AGAATCACAG
            CGTGCGTTCT  ATTTGTCGAG  CTCGGCTCTC  TGCGGCTCAA  ACTGCAATTC  TCTTAGTGTC
```

Fig. 2 cont.

```
      +1    P   A   Q   E     W   I   P     F   R   H     A   E   P   E     Q   V   D     S   C   F
     2881  CCAGCTCAAG AATGGATTCC TTTTAGACAC GCAGAGCCCG AGCAAGTCGA CAGTTGCTTT
           GGTCGAGTTC TTACCTAAGG AAAATCTGTG CGTCTCGGGC TCGTTCAGCT GTCAACGAAA

+1    A   T   P     C   K   R   C     E   R   G     H   G   V   D     D   I   E     D   F   W
     2941  GCGACGCCAT GCAAAAGATG CGAACGCGGC CATGGCGTCG ATGACATCGA GGACTTCTGG
           CGCTGCGGTA CGTTTTCTAC GCTTGCGCCG GTACCGCAGC TACTGTAGCT CCTGAAGACC

+1    S   N   E   G     Q   R   I     S   Y   H     L   K   G   Q     Q   K   V     M   D   P
     3001  TCGAACGAAG GCCAAAGAAT TCTTACCAC CTTAAGGGCC AGCAAAAAGT CATGGACCCC
           AGCTTGCTTC CGGTTTCTTA AGAATGGTG GAATTCCCGG TCGTTTTTCA GTACCTGGGG

+1    T   K   L     K   L   G     Q     G   I   S     A   H   E   K     C   A   N     I   A   L
     3061  ACCAAACTGA ACTTGGACA AGGTATCTCC GCGCATGAAA AATGCGCTAA CATTGCNCTC
           TGGTTTGACT TGAACCTGT TCCATAGAGG CGCGTACTTT TTACGCGATT GTAACGNGAG

+1    S   A   W     V   R   I   I     Q   D   Q     M   S   T   S     E   K   F     I   F   A
     3121  AGCGCGTGGG TGAGGATTAT CCAAGATCAG ATGAGCACGT CAGAGAAGTT CATCTTCGCG
           TCGCGCACCC ACTCCTAATA GGTTCTAGTC TACTCGTGCA GTCTCTTCAA GTAGAAGCGC

+1    N   G   Q   S     D   R   D     T   M   S     I   I   E   A     R   L   Q     E   K   A
     3181  AATGGGCAGT CAGACCGCGA TACCATGTCT ATCATTGAGG CACGCCTGCA GGAGAAGGCG
           TTACCCGTCA GTCTGGCGCT ATGGTACAGA TAGTAACTCC GTGCGGACGT CCTCTTCCGC

+1    R   E   F     K   S   I   D     I   K   E     F   D   T   V     H   N   W     V   S   I
     3241  CGGGAATTCA AATCTATAGA TATCAAGGAG TTCGATACGG TACATAACTG GGTCAGTATT
           GCCCTTAAGT TTAGATATCT ATAGTTCCTC AAGCTATGCC ATGTATTGAC CCAGTCATAA

+1    L   V   F     S   W   R     C     D   R   G     C   P   E   H     L   I   E     Y   F   E
     3301  CTTGTCTTCT CGTGGCGTTG CGACCGTGGG TGCCCAGAGC ACCTTATCGA GTATTTCGAG
           GAACAGAAGA GCACCGCAAC GCTGGCACCC ACGGGTCTCG TGGAATAGCT CATAAAGCTC

+1    K   R   S     K   S   R   T     L   S   S     R   I   G   S     V   D   V     S   F   M
     3361  AAACGCTCGA AAAGCCGGAC GCTCTCAAGC CGCATAGGAA GCGTCGACGT TAGCTTCATG
           TTTGCGAGCT TTTCGGCCTG CGAGAGTTCG GCGTATCCTT CGCAGCTGCA ATCGAAGTAC

+1    L   D   S   G     A   V   W     T   I   A     R   N   T   L     F   A   S     G   L   M
     3421  CTCGATTCTG GCGCTGTCTG GACCATTGCC AGAAACACCT TATTTGCCTC GGGTCTTATG
           GAGCTAAGAC CGCGACAGAC CTGGTAACGG TCTTTGTGGA ATAAACGGAG CCCAGAATAC

+1    L   A   L     F   V   G   V     D   F   I     A   A   K   G     D   D   V     F   L   A
     3481  CTCGCCCTTT TCGTCGGCGT CGATTTCATC GCGGCGAAAG GCGATGATGT CTTCCTCGCA
           GAGCGGGAAA AGCAGCCGCA GCTAAAGTAG CGCCGCTTTC CGCTACTACA GAAGGAGCGT

+1    G   N   N     L   Y   L   D     A   E   R     L   R   M   G     S   Y   L     A   A   N
     3541  GGGAATAATT TGTACTTGGA CGCAGAACGG CTTCGCATGG GATCTTACTT AGCCGCAAAC
           CCCTTATTAA ACATGAACCT GCGTCTTGCC GAAGCGTACC CTAGAATGAA TCGGCGTTTG
```

Fig. 2 cont.

```
        +1   N   L   K     I   E   K   T     A   V   V     S   F   I   G     F   I   V     S   Q   A
3601         AACTTGAAGA   TCGAGAAGAC   GGCGGTCGTG   AGCTTTATAG   GGTTTATCGT   TTCCCAAGCC
             TTGAACTTCT   AGCTCTTCTG   CCGCCAGCAC   TCGAAATATC   CCAAATAGCA   AAGGGTTCGG

+1   A   V   T     A   D   V   V     R   L   A     T   R   T   Y     G   R   S     Y   K   N
3661         GCCGTCACAG   CTGATGTCGT   GCGTCTAGCC   ACCCGGACTT   ACGGTCGAAG   TTATAAAAAC
             CGGCAGTGTC   GACTACAGCA   CGCAGATCGG   TGGGCCTGAA   TGCCAGCTTC   AATATTTTTG

+1   V   M   I   *
3721         GTGATGATCT   AGCGAGTATA   AGATAGCTAT   CGCTGACCAC   TGCAGTTGTT   TAGATCACCG
             CACTACTAGA   TCGCTCATAT   TCTATCGATA   GCGACTGGTG   ACGTCAACAA   ATCTAGTGGC

3781         AGAACTCGTC   TCATGACCGC   GATCAACTGC   GCCACCCTTT   ACGGCACCTC   GAAAGGTGCA
             TCTTGAGCAG   AGTACTGGCG   CTAGTTGACG   CGGTGGGAAA   TGCCGTGGAG   CTTTCCACGT
                                                                            p70 start
        +2                                                (SEQ ID NO:6)   M   S   D   L   H   L
3841         TCAATTATCT   GATGGACGCG   TTGGACGATT   CGGACACACT   AAAATGAGCG   ACCTACACTT
             AGTTAATAGA   CTACCTGCGC   AACCTGCTAA   GCCTGTGTGA   TTTTACTCGC   TGGATGTGAA +2   D   P   G     F   V   M   R     V   T   P     M   K   V     D   E   R     V   Y   S   G
3901         GGATCCCGGT   TTTGTCATGC   GGGTCACCCC   CATGAAGGTG   GACGAGCGGG   TTTATTCCGG
             CCTAGGGCCA   AAACAGTACG   CCCAGTGGGG   GTACTTCCAC   CTGCTCGCCC   AAATAAGGCC +2   Q   D   G     C   Q   R   A     D   K   T     R   E   K     Q   P   E     P   R   A   T
3961         ACAAGATGGA   TGCCAACGTG   CAGATAAGAC   CCGCGAGAAA   CAACCCGAAC   CAGGGCAAC
             TGTTCTACCT   ACGGTTGCAC   GTCTATTCTG   GGCGCTCTTT   GTTGGGCTTG   GTCCCGTTG +2   R   A   A     Q   T   T   T     T   T   S     T   Q   E     A   G   S     K   T   S   P
4021         CAGGGCCGCG   CAAACAACAA   CAACAACGTC   GACGCAGGAG   GCGGGGTCTA   AAACTTCCCC
             GTCCCGGCGC   GTTTGTTGTT   GTTGTTGCAG   CTGCGTCCTC   CGCCCCAGAT   TTTGAAGGGG +2   R   S   R     T   D   Y   Q     P   A   R     W   P   N     P   E   P     R   E   H   P
4081         CCGTAGTCGC   ACCGATTACC   AGCCCGCCAG   ATGGCCGAAC   CCCGAACCAC   GCGAACACCC
             GGCATCAGCG   TGGCTAATGG   TCGGGCGGTC   TACCGGCTTG   GGGCTTGGTG   CGCTTGTGGG +2   G   Q   P     R   S   D   T     R   E   G     A   K   A     S   D   D     G   E   S   H
4141         GGGTCAACCG   CGGTCGGACA   CGCGTGAGGG   GGCTAAGGCA   AGCGATGATG   GAGAGTCCCA
             CCCAGTTGGC   GCCAGCCTGT   GCGCACTCCC   CCGATTCCGT   TCGCTACTAC   CTCTCAGGGT +2   G   S   D     I   K   A   W     I   H   D     Y   L   D     P   D   G     E   Y   K   T
4201         TGGCAGCGAC   ATCAAGGCAT   GGATTCACGA   CTATCTAGAC   CCGGACGGAG   AATACAAGAC
             ACCGTCGCTG   TAGTTCCGTA   CCTAAGTGCT   GATAGATCTG   GGCCTGCCTC   TTATGTTCTG +2   S   L   D     D   G   K   I     P   D   G     A   I   P     Q   S   T     C   G   Q   F
4261         GAGCCTGGAC   GACGGGAAAA   TTCCCGACGG   CGCGATACCT   CAGTCAACAT   GCGGTCAATT
             CTCGGACCTG   CTGCCCTTTT   AAGGGCTGCC   GCGCTATGGA   GTCAGTTGTA   CGCCAGTTAA +2   R   G   T     V   G   A   R     Y   P   G     L   N   S     T   T   L     P   L   D   G
4321         TCGAGGGACC   GTGGGCGCCA   GATACCCGGG   ACTGAATTCT   ACGACGCTAC   CGCTGGATGG
             AGCTCCCTGG   CACCCGCGGT   CTATGGGCCC   TGACTTAAGA   TGCTGCGATG   GCGACCTACC
```

Fig. 2 cont.

```
         +2    G   T   W       P   L   L   V       M   H   L       P   F   F       R   H   P       L   F   I
      4381    CGGGACCTGG  CCTCTACTAG  TGATGCATCT  CCCGTTCTTC  AGGCATCCGT  TGTTGTTCAT
              GCCCTGGACC  GGAGATGATC  ACTACGTAGA  GGGCAAGAAG  TCCGTAGGCA  ACAACAAGTA

+2    T   T   T       S   N   T   E       V   E   V       T   N   A       D   L   D       A   F   A   N
      4441    CACCACCACC  AGCAACACGG  AAGTCGAAGT  GACGAACGCC  GATCTGGATG  CGTTCGCGAA
              GTGGTGGTGG  TCGTTGTGCC  TTCAGCTTCA  CTGCTTGCGG  CTAGACCTAC  GCAAGCGCTT

+2    D   W   N       N   R   T   D       W   T   E       A   T   Y       P   S   W       A   Q   V   G
      4501    CGATTGGAAC  AACAGGACGG  ACTGGACCGA  AGCGACGTAC  CCAAGTTGGG  CGCAAGTCGG
              GCTAACCTTG  TTGTCCTGCC  TGACCTGGCT  TCGCTGCATG  GGTTCAACCC  GCGTTCAGCC

+2    N   V   F       Y   M   V   V       P   T   E       A   L   T       D   V   P       P   P   T   Q
      4561    GAACGTGTTT  TACATGGTCG  TCCCGACCGA  AGCGCTGACG  GACGTACCAC  CCCCGACTCA
              CTTGCACAAA  ATGTACCAGC  AGGGCTGGCT  TCGCGACTGC  CTGCATGGTG  GGGGCTGAGT

+2    L   G   V       S   G   L   L       E   S   Y       R   L   T       S   S   G       V   T   A   Y
      4621    ACTGGGTGTA  TCAGGGTTAC  TCGAGAGTTA  CCGTCTGACA  TCGAGCGGCG  TCACAGCGTA
              TGACCCACAT  AGTCCCAATG  AGCTCTCAAT  GGCAGACTGT  AGCTCGCCGC  AGTGTCGCAT

+2    F   N   A       P   T   L   V       N   Q   G       V   A   V       I   A   Q       F   Q   P   D
      4681    CTTCAACGCA  CCCACTCTCG  TGAATCAGGG  AGTGGCGGTG  ATCGCGCAGT  TCCAACCGGA
              GAAGTTGCGT  GGGTGAGAGC  ACTTAGTCCC  TCACCGCCAC  TAGCGCGTCA  AGGTTGGCCT

+2    K   E   H       Q   K   E   N       P   D   I       V   A   G       T   T   Q       T   G   G   T
      4741    CAAAGAACAC  CAGAAGGAGA  ACCCGGACAT  AGTAGCCGGG  ACCACCCAAA  CGGGCGGAAC
              GTTTCTTGTG  GTCTTCCTCT  TGGGCCTGTA  TCATCGGCCC  TGGTGGGTTT  GCCCGCCTTG

+2    L   Q   L       G   G   S   G       P   N   Y       T   L   T       M   T   I       G   D   Q   V
      4801    GTTACAGCTC  GGCGGTTCAG  GGCCGAACTA  CACATTGACG  ATGACGATCG  GGGACCAGGT
              CAATGTCGAG  CCGCCAAGTC  CCGGCTTGAT  GTGTAACTGC  TACTGCTAGC  CCCTGGTCCA

+2    E   F   G       G   A   A   I       P   L   P       T   V   S       M   G   P       M   P   E   S
      4861    CGAGTTCGGG  GGCGCAGCAA  TCCCGCTACC  CACGGTGTCG  ATGGGGCCGA  TGCCGGAGTC
              GCTCAAGCCC  CCGCGTCGTT  AGGGCGATGG  GTGCCACAGC  TACCCCGGCT  ACGGCCTCAG

+2    G   Q   L       V   F   Q   T       A   N   L       T   F   D       V   G   N       T   I   T   I
      4921    GGGGCAGCTG  GTGTTCCAGA  CTGCAACCT   GACATTCGAC  GTCGGAAACA  CAATCACCAT
              CCCCGTCGAC  CACAAGGTCT  GACGTTGGA   CTGTAAGCTG  CAGCCTTTGT  GTTAGTGGTA

+2    T   T   T       L   P   P   G       S   V   T       G   M   W       Q   F   T       A   S   N   G
      4981    CACGACCACG  CTGCCACCAG  GGTCGGTGAC  GGGAATGTGG  CAATTCACAG  CCAGCAACGG
              GTGCTGGTGC  GACGGTGGTC  CCAGCCACTG  CCCTTACACC  GTTAAGTGTC  GGTCGTTGCC

+2    T   D   T       V   T   V   D       A   G   A       T   V   R       V   R   S       E   F   G   R
      5041    GACGGACACC  GTGACCGTGG  ACGCGGGAGC  GACTGTACGC  GTTCGGAGCG  AATTTGGACG
              CTGCCTGTGG  CACTGGCACC  TGCGCCCTCG  CTGACATGCG  CAAGCCTCGC  TTAAACCTGC
```

Fig. 2 cont.

```
      +2   L   G   T     E   S   A   G     H   Q   L     N   Q   D     S   T   N     D   M   N   P
    5101   CCTCGGAACT   GAATCTGCAG   GACATCAACT   CAATCAAGAT   TCCACCAACG   ACATGAACCC
           GGAGCCTTGA   CTTAGACGTC   CTGTAGTTGA   GTTAGTTCTA   AGGTGGTTGC   TGTACTTGGG

+2   N   D   A     G   N   A   K     T   I   Q     F   Q   L     T   K   R     G   H   Y   M
    5161   AAATGATGCA   GGCAACGCCA   AGACCATTCA   GTTCCAACTA   ACGAAACGAG   GCATTATAT
           TTTACTACGT   CCGTTGCGGT   TCTGGTAAGT   CAAGGTTGAT   TGCTTTGCTC   CGTAATATA

+2   P   E   A     S   I   R   V     R   N   D     N   A   T     S   Y   G     P   V   D   E
    5221   GCCTGAGGCG   TCAATCCGTG   TTCGAAATGA   CAATGCGACG   TCTTATGGAC   CGGTCGATGA
           CGGACTCCGC   AGTTAGGCAC   AAGCTTTACT   GTTACGCTGC   AGAATACCTG   GCCAGCTACT

+2   D   T   E     D   N   C   G     R   L   H     R   A   I     G   A   L     Q   G   Y   H
    5281   AGACACCGAG   GACAACTGTG   GTAGATTACA   CCGGGCAATT   GGTGCACTCC   AAGGATACCA
           TCTGTGGCTC   CTGTTGACAC   CATCTAATGT   GGCCCGTTAA   CCACGTGAGG   TTCCTATGGT

+2   R   Q   Q     L   R   D   R     L   P   S     M   T   G     M   S   T     S   V   P
    5341   TCGACAGCAA   CTTCGCGATA   GGTTGCCGTC   GATGACCGGT   ATGTCTACAT   CAACCGTACC
           AGCTGTCGTT   GAAGCGCTAT   CCAACGGCAG   CTACTGGCCA   TACAGATGTA   GTTGGCATGG

+2   Y   L   Q     G   V   P   T     L   R   S     D   T   G     G   E   P     W   G   P
    5401   CTACTTGCAA   GGTGTTCCGA   CGCTTCGAAG   CGATACCGGC   GGAGGGGAGC   CTTGGGGCCC
           GATGAACGTT   CCACAAGGCT   GCGAAGCTTC   GCTATGGCCG   CCTCCCCTCG   GAACCCCGGG

+2   F   A   S     A   T   P   P     K   D   D     V   A   L     T   V   A   R     T   W   T
    5461   CTTCGCTAGT   GCGACACCTC   CGAAGGACGA   CGTGGCGCTA   ACAGTGGCTC   GAACTTGGAC
           GAAGCGATCA   CGCTGTGGAG   GCTTCCTGCT   GCACCGCGAT   TGTCACCGAG   CTTGAACCTG

+2   D   L   H     P   F   A   Y     P   E   R     Y   N   G     F   G   A   L     F   A   M
    5521   CGATCTGCAC   CCATTCGCAT   ACCCGGAACG   ATACAACGGA   TTCGGGGCCC   TATTCGCGAT
           GCTAGACGTG   GGTAAGCGTA   TGGGCCTTGC   TATGTTGCCT   AAGCCCCGGG   ATAAGCGCTA

+2   V   A   K     T   I   A   Q     I   P   R     Y   V   R     S   A   A   G     V   A   N
    5581   GGTGGCCAAG   ACCATAGCCC   AGATACCTCG   CTATGTGCGA   TCAGCAGCCG   GAGTGGCGAA
           CCACCGGTTC   TGGTATCGGG   TCTATGGAGC   GATACACGCT   AGTCGTCGGC   CTCACCGCTT

+2   A   V   T     D   C   I   E     S   A   T     E   S   V     A   S   N     S   T   S   E
    5641   TGCGGTGACG   GACTGCATAG   AGAGCGCGAC   CGAGAGTGTA   GCCTCGAATT   CCACCTCGGA
           ACGCCACTGC   CTGACGTATC   TCTCGCGCTG   GCTCTCACAT   CGGAGCTTAA   GGTGGAGCCT

+2   R   R   Q     R   R   A   R     R   V   G     G   I   A     R   G   A   R     N   L   V
    5701   GAGGCGGCAA   CGAAGAGCGA   GACGTGTTGG   CGGAATCGCT   CGAGGAGCCC   GCAATCTTGT
           CTCCGCCGTT   GCTTCTCGCT   CTGCACAACC   GCCTTAGCGA   GCTCCTCGGG   CGTTAGAACA

+2   G   R   I     G   N   L   S     L   *
    5761   GGGCCGCATA   GGGAACCTTA   GCTTGTAGGT   TCATTGCGAC   ATGGGATGTT   CTTCAGTCAG
           CCCGGCGTAT   CCCTTGGAAT   CGAACATCCA   AGTAACGCTG   TACCCTACAA   GAAGTCAGTC
```

Fig. 2 cont.

```
5821  CAGCTCTTCG GTTTCATCTC CACTGACGAC CCTCTGCACG TATTTTCCCA TCATCGTGGT
      GTCGAGAAGC CAAAGTAGAG GTGACTGCTG GGAGACGTGC ATAAAAGGGT AGTAGCACCA

5881  GCTGATCATC ATTTGCGGTC TGGTTTGGCT CGCTTCCTAT TGTTTTCATG GCAGATCAAC
      CGACTAGTAG TAAACGCCAG ACCAAACCGA GCGAAGGATA ACAAAAGTAC CGTCTAGTTG

5941  TCGACCCAAT CGAAATCTTC ATCGAATTCC TCGGATTTCG AAAGATTTCC GGAGCCATTC
      AGCTGGGTTA GCTTTAGAAG TAGCTTAAGG AGCCTAAAGC TTTCTAAAGG CCTCGGTAAG

6001  GCTGCTTCCA GTGTAAGCAA GTCTTGGGAC CTGCAGGACC CGTGGATTCC CACCTCACTG
      CGACGAAGGT CACATTCGTT CAGAACCCTG GACGTCCTGG GCACCTAAGG GTGGAGTGAC

6061  ATTGTCAGTG GAAGGCCGCG GTGTTAAATC TTATTAACAA TCAGCTTTAC GACGTCGATA
      TAACAGTCAC CTTCCGGCGC CACAATTTAG AATAATTGTT AGTCGAAATG CTGCAGCTAT

6121  TCGATGAGAC GAATCCGTTT CTTTACGGAC CTCACCGCGA CTGAGATGTG GAAGACCACA
      AGCTACTCTG CTTAGGCAAA GAAATGCCTG GAGTGGCGCT GACTCTACAC CTTCTGGTGT

6181  TTGTTCCTTC ACACATGCCC AGAGTGCGGT TATTCCACCA GGGACACAGA AACTACGAGA
      AACAAGGAAG TGTGTACGGG TCTCACGCCA ATAAGGTGGT CCCTGTGTCT TTGATGCTCT

6241  TCGTGTCCCC GAGATTGCCA AGACGGCAAT CTTATGCACG CATCTTCGGT CGGCTATATT
      AGCACAGGGG CTCTAACGGT TCTGCCGTTA GAATACGTGC GTAGAAGCCA GCCGATATAA

6301  TGTCACAAAT GCCGGTTAGA AGCAAACACA TTTTACCACG GTTTATGCTC TCAGTGTCGC
      ACAGTGTTTA CGGCCAATCT TCGTTTGTGT AAAATGGTGC CAAATACGAG AGTCACAGCG

6361  GACCGTGATA ATAAAAAACG ACGCTGAAGA GAGGACTCAC AACTACCTCG ATCTCGTTTA
      CTGGCACTAT TATTTTTTGC TGCGACTTCT CTCCTGAGTG TTGATGGAGC TAGAGCAAAT

6421  TCGGACGAGT GATACAATTG ACCCAGGGTC ATCCTGCAAA ACACGCAGGT TTCCGATAGT
      AGCCTGCTCA CTATGTTAAC TGGGTCCCAG TAGGACGTTT TGTGCGTCCA AAGGCTATCA

6481  GGTGCAAATC CACCCGCCAG TCGTCGGTGG TCCCTTGCGG GACCTATACG GTACCA
      CCACGTTTAG GTGGGCGGTC AGCAGCCACC AGGGAACGCC CTGGATATGC CATGGT
```

MODIFIED SMALL RNA VIRUSES

FIELD OF THE INVENTION

This invention relates to small RNA viruses and virus-like particles (VLPs) having altered or substituted Ig-like domains so as to modify host cell tropism or, in other words, the specificity of host cell binding and infection. The invention also relates to the use of such small RNA viruses and VLPs in insecticidal and medicinal applications.

BACKGROUND TO THE INVENTION

Formally recognised small RNA viruses include members of Picornaviradae, the Nodaviradae and the Tetraviradae. However, there are many unrecognised insect viruses that also fall into this category. The Tetraviradae are a family of small isometric insect viruses with unenveloped, icosahedral capsids 35–41 nm in diameter and single-stranded positive-sense RNA (ss+RNA) genomes. They have not received wide attention from virologists. Their known host range is confirmed to only a few families of moths in a single insect order, the Lepidoptera (moths, butterflies), making them the only small RNA virus family restricted to insect hosts. While they appear to be effective at controlling several of their hosts that are important insect pests, they have been little used in this regard. The lack of a cell culture system or, until recently, a reliable means to obtain the virus from laboratory reared insects made it necessary to rely on sporadically available field-collected material of uncertain quality. Such was the difficulty that only recently did it emerge that there are actually two groups of tetraviruses, Nudaurelia β-like viruses having a mono-partite genome of ca. 6 kb and Nudaurelia ω-like viruses having a bi-partite genome comprising ss RNAs of 5.3 and 2.5 kb. There are only two known Nudaurelia ω-like viruses. The complete genome of one member (*Helicoverpa armigera* stunt virus—HaSV) has been previously sequenced by the present inventors. The other member is Nudaurelia ω virus (NωV) which has been partially sequenced.

One of the most intriguing aspects of infections by tetraviruses is that they appear only to infect a single tissue type, which in the case of HaSV is the midgut. In a definitive experiment that highlights the specificity of HaSV, the present inventors showed that its midgut specificity prevailed even when virus was injected into the haemocoel of larvae, thereby exposing host non-midgut cell types not normally exposed to HaSV. The presence of virus was examined by using cloned cDNA probes on Northern blots of RNA extracted from midguts and from the rest of the carcasses from three groups of larvae, one injected with HaSV, one fed HaSV and uninfected controls. They observed a positive signal only in the midgut RNA of both groups of larvae treated with HaSV.

Further evidence for specific binding of HaSV particles to a particular cell type comes from a rigorous examination of larvae of *H. armigera* infected with HaSV. The sensitive immuno-histochemistry technique of immuno-gold staining with silver enhancement was employed on a series of cross- and sagittal-sections of infected larvae. Sections in this series were also examined with electron microscopy. Staining appeared only in midgut cells despite close attention to tissues from the foregut, fat body, salivary gland, and brain. Both types of differentiated cells of the midgut, the columnar and goblet cells, were found to be infected, as were the much smaller undifferentiated regenerative cells at the basal membrane. Although all these midgut cell types were found to be infected, analysis of virus binding to cells in sections of wax-embedded midgut showed that only goblet cells, and not columnar cells, were the primary target of HaSV binding.

The two known ω-like viruses show a high degree of sequence identity. That is, the amino acid sequences of the coat proteins of the two ω-like viruses show an overall 67% identity (76% similarity). This comparison defined four domains in the coat (capsid) protein, with two regions of high homology (ca. 80% identity and containing extensive stretches of sequence reaching over 95% identity) (Hanzlik et al., 1995). A 49 residue amino-terminal domain shows lower homology, as does a 165 residue sequence located towards the middle of the sequence and showing 33% identity. Surprisingly, the high overall sequence identity is not reflected in a detectable serological relationship suggesting that the central domain of low sequence homology is exposed on the capsid surface as the sole immunogenic portion of the intact virion. As first suggested by Hanzlik et al. (1995), this region is responsible for the differing host specificities of the two viruses.

The present inventors have now surprisingly realised that the central domain (corresponding to residues 287 to 416) of HaSV forms a structure belonging to the Immunoglobulin (Ig) superfamily. Other protein domains whose structures show an Ig-like fold include the variable (V) and constant (C) domains found on antibodies (e.g. the Fab fragment of IgGs), the HLA surface antigens of the MHC complex and cell adhesion proteins and receptors (e.g. the CD4 receptor recognised by HIV gp 120). Mediation of cell adhesion to other cells or the extracellular matrix by these proteins is central to development, differentiation, the immune response and tissue structure and healing. Many of these proteins are also used as receptors by viruses (Lentz (1990).

Recent studies based on cell adhesion assays and analysis of artificial lipid bilayers attached to plates have elucidated the basis of cell adhesion promoted by binding of surface proteins. These studies are exemplified by work on the binding between the MHC class II and CD4 proteins, which mediate adhesion of antigen presenting cells (APCs) and $CD4^+$ T cells in the immune response. Soluble (monomeric) CD4 (sCD4) fails to inhibit the MHC class II-specific proliferative response of T-cell clones (Hussey et al., 1988) or the binding of MHC class $II^+$ B cells to CD4-transfected COS-7 cells in cell adhesion assays, even at a concentration of 100 $\mu$M (Sakihama et al., 1995a). This implies that the affinity of the monomeric sCD4 for the MHC class II proteins is $>10^{-4}$M. It has now been shown that oligomerization of CD4 molecules on the surface of $CD4^+$ cells is required for stable binding to MHC class II proteins, by increasing the avidity of the interaction between these cell adhesion protein molecules (Sakihama et al., 1995 a,b). This oligomerization follows an initial interaction between 1 or 2 CD4 molecules and MHC class II dimers. Characterization of chimaeric CD4 molecules has shown that the membrane proximal domains 3 and/or 4 appear to be involved in oligomerization.

The present inventors have now recognised that the lack of sequence similarity between the Ig-like domain of HaSV and the corresponding domain of NωV may allow tetravirus particles to be used as icosahedral platforms capable of carrying altered Ig-like domains or substituted tertiary structures and thereby show modified host cell binding specificities.

The Ig-like domain forms a prominent protrusion which interacts with either quasi 3-fold or icosahedral 3-fold related subunits on the surface of the tetravirus capsid. The icosahedral particles therefore present a defined oligomeric form of the Ig-like domain which is likely to allow stable binding of the complete capsid to the cell-surface receptor, analogous to the binding between CD4 and MHC class II oligomers. Support for this notion comes from the findings of Weber and Karjalainen (1993), who reported that a soluble, pentameric immunofusion construct of mouse CD4 and human $C\mu$ could inhibit the interaction between polymer-bound mouse sCD4 and B cells, whereas a soluble monomeric immunofusion construct of mouse CD4 and mouse Cκ could not.

DISCLOSURE OF THE INVENTION

Thus, in a first aspect, the present invention provides an isolated small RNA virus of a kind which includes an Ig-like domain within the wild-type coat protein(s), wherein said Ig-like domain has been altered or substituted so as to modify host cell tropism.

By "Ig-like domain" we refer to a distinct structural domain having a core structure with seven to nine antiparallel β-strands forming a "barrel-like" shape however, since hydrogen bonds do not extend around the barrel, there is, in effect, two distinct β-pleated sheets and physically the fold is a β-sandwich (Bork et al. 1994). Some Ig-like domains within this definition (such as the tetravirus Ig-like domain), may also have additional β-strands outside of the core structure.

By "host cell tropism" we refer to the capacity of viruses (and virus-like particles (VLPs) as described below) to bind, enter and commence infection in specific populations of cells within an organism.

Preferably, the Ig-like domain is altered such that the virus selectively binds and infects a predetermined cell type which is other than the virus' normal host cell type(s). Such "targeting" enables, for example, the utilisation of the small RNA virus' insecticidal properties in the control of pest insects outside of the normal host species range. Small RNA viruses according to the invention thereby offer significant potential as insecticidal agents.

Whilst the invention is particularly described in relation to Tetraviradae, it is anticipated that Ig-like domains are also located in other small RNA viruses. Accordingly, the small RNA virus of the first aspect is selected from members of Picornaviradae, the Nodaviradae and the Tetraviradae. Preferably, the small RNA virus is a member of the Tetraviradae family such as a Nudaurelia β-like virus (particularly NβV). More preferably, the small RNA virus is a member of the genus of Nudaurelia ω-like viruses. Most preferably, the small RNA virus is selected from *Helicoverpa armigera* stunt virus (HaSV) and Nudaurelia ω virus (NωV).

The Ig-like domain of the HaSV wild-type coat protein (p71) is located at residues 281 to 414 of the amino acid sequence shown at FIG. 1. The Ig-like domain of the NβV wild-type coat protein is located within residues 285 to 433 of the 634 amino acid sequence shown at FIG. 2. The Ig-like domain of the NωV wild-type coat protein is located at residues 280 to 413 of the sequence reported by Agrawal and Johnson, 1995.

Alterations or substitutions of the Ig-like domain may be achieved by replacing the wild-type coat protein gene(s) with a chimaeric gene(s) including nucleotide sequences encoding all or a functional portion(s) of Ig-like domains derived from other proteins such as those mentioned above. Functional portion(s) in this context refers to portion(s) of Ig-like domains which still permit the small RNA virus to specifically bind and infect one or more cell types.

For targeting the small RNA virus to cell types of pest insects outside of the normal host species range, the chimaeric gene(s) may include nucleotide sequences encoding all or a functional portion(s) of the variable (V) or constant (C) domains of antibodies specific to gut cell types belonging to the target pest insect. Alternatively, the chimaeric gene(s) may include nucleotide sequences encoding all or a functional portion(s) of Ig-like domains derived from proteins involved in cell adhesion or monoclonal antibodies specific for cell surface epitopes.

Whilst it is preferred to alter or substitute the Ig-like domain using nucleotide sequences encoding Ig-like domains or functional portion(s) thereof derived from other proteins, it is to be understood that the invention contemplates alteration and substitution of the Ig-like domain using nucleotide sequences encoding non-Ig-like tertiary structures so as to achieve favourable modification of host cell tropism. For example, the Ig-like domain may be altered by inclusion of, or substituted with, a peptide loop (e.g. such as those present on the coat protein of nodaviruses), small protein or lectin.

Suitable alterations of the Ig-like domain might also be achieved with techniques such as site-directed mutagenesis of the wild-type coat protein gene(s).

In a second aspect, the present invention provides a method for controlling the proliferation of a pest insect, comprising applying to an area infected with said pest insect a small RNA virus according to the first aspect, optionally in admixture with an agriculturally acceptable carrier.

The coat proteins from both NωV and HaSV have the ability to form virus like particles (VLPs) when expressed in a baculovirus expression system. The findings of the present inventors therefore offer the possibility of producing VLPs for use as specific delivery agents of, for example, nucleic acid molecules. These VLPs may therefore be useful as insecticidal agents or for use as a means of specific gene delivery for, for example, gene therapy. The production of VLPs from small RNA viruses is discussed in International Patent Application No. PCT/AU93/00411, the entire disclosure of which is to be regarded as incorporated herein by reference.

The HaSV VLPs have properties highly similar to those of HaSV virions. These include resistance to proteolytic degradation, buoyancy in CsCl solutions, morphology and dimensions, ability to protect encapsidated RNA from degradation, and affinity to the *H. armigera* gut cell receptor for HaSV. The latter property was demonstrated by the observation that VLPs bound in an identical manner to receptors on *H. armigera* gut cells in wax cross sections of larvae. This indicates that VLPs will be able to enter the cells and express RNAs within them.

Thus, in a third aspect, the present invention provides a virus-like particle (VLP) prepared from expression of a coat protein gene(s) derived from a small RNA virus of a kind which includes an Ig-like domain within the wild-type coat protein(s), said gene(s) having been altered such that the Ig-like domain of the expressed coat protein is altered or substituted so as to modify host cell tropism.

Preferably, the VLP is prepared from expression of a coat protein gene(s) which has been altered such that the Ig-like domain of the expressed coat protein is altered or substituted such that the VLP selectively binds and infects a predetermined cell type(s) which is other than a host cell type(s) which the VLP, absent the alteration or substitution of the Ig-like domain of its coat protein(s), would bind and infect.

Preferably, the coat protein gene(s) is derived from a member of Picornaviradae, the Nodaviradae and the Tetraviradae. However, preferably, the gene(s) is derived from a member of the Tetraviradae family such as Nudaurelia β-like virus (particularly NβV). More preferably, the gene(s) is derived from a member of the genus of Nudaurelia ω-like viruses. Most preferably, the gene(s) is derived from *Helicoverpa armigera* stunt virus (HaSV) or Nudaurelia ω virus (NωV).

The coat protein gene(s) used to express the VLP may be produced by replacing the wild-type coat protein gene(s) with a chimaeric gene(s) as described above in regard to the first aspect.

VLPs according to the third aspect of the present invention offer significant potential for specifically delivering nucleic acid molecules to a predetermined cell type(s). For use as insecticidal agents, the nucleic acid may, for example, encode a toxin such as ricin, neurotoxins, gelonin and diptheria toxins. In medicinal applications, the nucleic acid molecules may, for example, encode a cytotoxin (e.g. for cancer treatment) or other peptide, polypeptide or protein as required (e.g. for gene therapy).

Although the inventors have observed, on occasion, that VLPs from the HaSV coat protein will encapsidate low molecular weight RNA having no virus sequences, it is probably necessary that encapsidation (and replication) signal sequences on the virus RNA be utilised, if the VLPs of the third aspect are to be useful for delivering desired genes to target cells. That is, it is probably necessary that encapsidation (and replication) signals be utilised to allow production of VLPs which specifically encapsidate and deliver expressible RNA of exogenous origin, thereby enabling the delivery of desirable activities to target cells. This may be in the form of an mRNA to produce a functional protein when translated in the target cell or in the form of retroviral or retrotransposon RNA which will be incorporated into the target cell genome from which the product will eventually be expressed.

The possibility of altering or substituting the Ig-like domain of small RNA virus coat proteins also offers the development of VLPs carrying antigenic tertiary structures. Such VLPs would offer considerable promise as vaccination agents.

Thus, in a fourth aspect, the present invention provides a vaccine comprising a virus-like particle (VLP) prepared from expression of a coat protein gene(s) derived from a small RNA virus of a kind which includes an Ig-like domain within the wild-type coat protein(s), said gene(s) having been altered such that the Ig-like domain of the expressed coat protein is altered or substituted so that the VLP presents a surface located antigen to elicit an immune response in a host organism.

The antigen may be all or an antigenic portion of a protein from, for example, a virus (e.g. HIV, HCV, CMV) or bacteria (e.g. Mycobacocus, Streptococcus, Haemophilias).

From studies conducted on tetravirus coat proteins and VLPs, the present inventors have identified a unique group of six properties or characteristics which enable the production of the specific RNA delivery VLPs contemplated by the present invention. These characteristics may be summarised as:

1. The ability of tetravirus coat proteins when expressed from exogenous expression systems to readily produce VLPs.
2. The ability of tetravirus VLPs to readily encapsidate exogenous mRNAs including viral encapsidation signal sequences and encoding peptides, polypeptides and proteins of differing activities.
3. The ability of tetravirus VLPs to be able to deliver exogenous mRNAs in such a manner that translation of encoded peptides, polypeptides or proteins occurs specifically in the cells to which the VLPs bind and infect.
4. The provision within the tetravirus coat proteins of a distinct region that forms an Ig-like domain responsible for host cell tropism.
5. The possibility of modifying or substituting the Ig-like domain on tetravirus coat proteins with other Ig-like domains and structures of exogenous origin.
6. The possibility of producing tetravirus VLPs exhibiting low reactivity to the vertebrate immune system.

These characteristics and the feasibility of producing specific RNA delivery VLPs is described in greater detail below with reference to the following, non-limiting examples and accompanying figures.

BRIEF DESCRIPTION OF THE FIGURES

FIG. 1 provides the nucleotide sequence of a cDNA (SEQ ID NO:1) encoding RNA 2 of the HaSV genome (the nucleotide sequence of a cDNA encoding RNA1 is provided in the abovementioned Patent Application No. PCT/AU93/00411). The putative amino acid sequences of the coat proteins p71 (SEQ ID NO:2) and p17 (SEQ ID NO:3) are also shown. p71 includes an Ig-like domain at residues G281 to E414.

FIG. 2 provides the nucleotide sequence of a cDNA (SEQ ID NO:4) encoding the NβV RNA genome. The putative amino acid sequences of encoded proteins is also provided (SEQ ID NOS:5 and 6). The coat protein (p70) includes an Ig-like domain at residues P285 to K433 of the 634 residue sequence.

EXAMPLE 1

VLP production from exogenous expression systems:

The tetravirus coat proteins easily produce VLPs after being expressed by exogenous expression systems, and importantly, they assemble into RNA-containing VLPs under in vitro conditions. In vitro assembly facilitates inexpensive, large scale production of VLPs carrying mRNAs encoding a variety of desired peptides, polypeptides or proteins and including cytotoxins which would be expected to hamper in vivo production due to their toxicities towards the host. In vitro production of VLPs may also be of importance in medicinal applications, since it should be possible to readily meet the stringent requirements for elimination of contaminating organisms/factors.

In vivo production of tetravirus VLPs in eukaryotic expression systems such as baculoviruses, yeast and plant cells is described in the abovementioned International Patent Specification No. PCT/AU/93/00411, and Hanzlik and Gordon, 1997. Briefly, the production of tetravirus VLPs in these systems involves the expression of the coat protein precursor gene (e.g. for HaSV; p71 of RNA2) with a strong promoter, then purifying the VLPs as for HaSV virions or by the procedure of Agrawal and Johnson (1995). To produce tetravirus VLPs under in vitro conditions, a procedure described by Yusibov et al. (1996) may be used after expression of the coat protein precursor in a prokaryotic host such as *E. coli*.

EXAMPLE 2

Production of HaSV VLPs encapsidating exogenous RNA:

The VLPs produced from tetravirus coat proteins readily incorporate exogenous mRNAs having certain viral encapsidation signal sequences. Such mRNAs may encode a variety of desired peptides, polypeptides and proteins. This can be demonstrated by the following experiment which places the nonviral gene, *E. coli* β-glucuronidase (GUS) within HaSV VLPs.

HaSV VLPs having translatable GUS mRNA within them can be made by coinfecting Sf9 cells with two recombinant baculoviruses. Using the commercially available baculovirus vector, pFastBac of the Bac-to-Bac Expression System (Gibco-BRL). Baculovirus 1 was constructed by placing the p71 coat protein open reading frame (ORF) (see FIG. 1) behind the polyhedrin promoter. When Baculovirus 1 infects Sf9 cells by itself, VLPs are formed which selectively encapsidates the transcribed mRNAs of the coat protein ORF. This indicates that an encapsidation signal sequence is within the coat protein ORF. This information was used to construct Baculovirus 2 which produced an encapsidatable RNA that expressed GUS activity.

Baculovirus 2 or pFBGUSp71 virus was constructed by placing the GUS ORF (β-glucuronidase, Jefferson et al., 1986) between the coat protein ORF and the polyhedrin promoter so that the initiating AUG codon would start translation of the GUS ORF instead of the coat protein ORF. Thus, when transcription occurs during the baculovirus infection, mRNA is produced that is expressed as GUS. This mRNA also possesses the encapsidation signal sequences possessed by the HaSV p71 coat protein ORF placed behind the GUS ORF. Consequently, when Baculoviruses 1 and 2 infect the same cell, VLPs made from Baculovirus 1 selectively encapsidate RNAs with the coat protein ORF only as well as those RNAs with the GUS ORF followed by the coat protein ORF.

Encapsidation of the GUS mRNA is confirmed by Northern blotting of RNA extracted from purified VLPs produced from Sf9 cells coinfected with both baculoviruses. To purify the VLPs, Sf9 cells are infected with the two viruses and after four days the cells are lysed with freeze/thaw and vortexing in Tris buffer (50 mM Tris pH 7.4) with 0.2% Nonidet P40 detergent. After clarification at 10,000×g for 10 minutes, the supernatant of homogenate is pelleted through a 10% sucrose cushion at 100,000×g for three hours. The pellet, resuspended by an overnight incubation, is directly layered onto a centrifuge tube having equal volumes of 30% and 60% CsCl in Tris buffer which is then spun at 200,000×g for 12 hours. The opalescent band is then pelleted at 100,000×g for three hours then resuspended in Tris buffer. When the extracted RNA is probed with a radioactively labelled GUS only probe, the RNA from the VLPs hybridises strongly to a 4.6 kb band, which is the size of the expected mRNA transcribed from the pFBGUSp71 virus. These GUS RNA containing VLPs also bind to *H. armigera* midgut cells in a manner highly similar to HaSV virions. This is seen when the particles are incubated with wax cross-sections of *H. armigera* midguts and immunologically detected according to the procedure of Bravo et al. (1992).

Alternative constructions of Baculovirus 2 could have included all of the HaSV RNA2 (FIG. 1) placed behind the GUS ORF, or the GUS ORF placed within RNA2 with the initiating AUG codon located at the site of the initiating AUG codon of either the p17 or p71 ORFs.

VLPs containing almost any mRNA can be made in vitro by first transcribing capped RNA in vitro with T7 polymerase then assembling the transcripts with purified coat proteins as described by Yusibov (1996).

EXAMPLE 3
Delivery of exogenous RNA encapsidated in HaSV VLPs:
Tetravirus VLPs are able to deliver encapsidated mRNAs for translation specifically in cells to which they bind and infect. This phenomenon has been observed by feeding GUS mRNA containing VLPs made in accordance with Example 2 from HaSV p71, to neonate larvae of *H. armigera*.

A 10% sucrose solution with 100 μg/ml (mRNA) concentration of GUS VLPs were fed to neonate larvae with the droplet feeding method (Hughes and Wood, 1981) and then sacrificed after three hours at room temperature. Eleven (11) GUS VLP-fed larvae were collected and separately homogenized in GUS extraction buffer Jefferson et al., 1986) with 1 mM X-Gluc (50 mM $NaHPO_4$, pH 7.0, 5 mM dithiothreitol, 1 mM $Na_2EDTA$, 0.1% triton X-100). A distinct blue colour indicating the presence of GUS, developed overnight in the extract, whilst a similar extract obtained from control larvae (11) fed VLPs without GUS mRNA, remained colourless. The result was confirmed by excising the midguts of the neonate larvae fed GUS mRNA containing VLPs and placing them into X-Gluc assay buffer (2 mM X-Gluc, 50 mM $NaHPO_4$, pH 7.0, 0.1% triton X-100). After incubation overnight, a blue spot occurred directly behind the stromadeal valve indicating GUS activity. The controls failed to show any blue colour.

EXAMPLE 4
Substituting the Ig-like domain of HaSV and NωV VLPs:
Tetravirus coat proteins have a distinct region in the amino acid sequence that forms a domain on the surface of the VLP which is responsible for host cell tropism. X-ray crystallography studies indicate that this domain has a immunoglobulin-like (Ig-like) tertiary structure (Munshi et al., 1996). The importance of the Ig-like domain in host cell tropism is made evident by the following experimentation which show that the HaSV Ig-like domain binds highly specifically to a factor in the midgut goblet cell cavity.

*H. armigera* midguts were excised and embedded in wax then sectioned by standard procedures. HaSV virions and GUS VLPs produced according to Example 2 were then incubated with the sections for 30 min, washed and then histochemically tested for the presence of HaSV virions or VLPs according to method of Bravo et al. (1992). The results obtained showed that specific binding of HaSV VLPs occurs only to the goblet cell factor. No binding occurs on other tissues or cultured cells. In addition, no binding of HaSV VLPs occurs to other lepidopteran midguts such as *Nudaurelia cyntheria capensis* or *Galleria melonella*.

Experimentation also showed that the binding is saturable. This was observed by a double label experiment using HaSV virions and GUS VLPs labeled with photo-biotin (Bresatec) in accordance with the supplier's instructions, and detected with avidin reagents according to standard procedures. Biotin labelled particles incubated with midgut wax sections were only detected in the absence of a 30 min preincubation with unlabelled HaSV VLPs.

In further experimentation involving the wax section binding assay described above, it was shown that the HaSV Ig-like domain is responsible for binding activity. This was achieved by producing hybrid Nudaurelia ω virus (NωV) VLPs having the Ig-like domain of HaSV, thereby conferring to the NωV VLPs the identical, specific binding activity to *H. armigera* midgut goblet cells as that of HaSV virions and VLPs. Furthermore, the hybrid particles were able to deliver GUS mRNA having the NωV RNA2 sequence (Agrawal and Johnson, 1992) on the transcript 3' to the GUS ORF. This was also shown in a complementary experiment where HaSV hybrid particles with the Ig-like domain of NωV showed specific binding to Nudaurelia midguts not shown by HaSV VLPs.

The NωV hybrid particles with the HaSV Ig-like domains were made by placing the NωV coat protein ORF (Agrawal and Johnson, 1995) into the baculovirus expression vector, pFastBac (Gibco-BRL) to generate pFBWCAP and performing the seamless cloning procedure described by Padgett and Sorge (1996). Primer Omega1 (ATGACTCTTCTCTGTGTGGTGGCGATCGGAGTAAG) (SEQ ID NO:7) and primer Omega2 (AGTACTCTTCAACTACCGCTGCTTCTAATCGCAG) (SEQ ID NO:8) were used to produce a 6.4 kb PCR fragment from pFBWCAP and having the vector containing the N-terminal and C-terminal regions of the coat protein ORF prior to and after the Ig-like domain (from residues M1-Q274 and T415-stop 445). Similarly, a 428 bp fragment having residues Q277-T420 of the HaSV coat protein was produced by PCR with Pfu polymerase from Primers StuntIgN (AGTACTCTTCGCAGTACGACGTCAGCGAGGCCGAC) (SEQ ID NO:9) and primerStuntIgC, (ATGACTCTTCGAGTCTCTAAGAGCGTGTTCCTAAA) (SEQ ID NO:10). Both fragments were digested with Eam 1104 I and ligated to form plasmid pFBWIg. This plasmid was then used to produce a recombinant baculovirus according to the supplier (Gibco-BRL) of the Bac-to-Bac baculovirus expression system. The resulting hybrid VLPs were prepared from Sf9 cells infected with the recombinant baculovirus by the procedure used to prepare HaSV VLPs in Example 2.

EXAMPLE 5

Modification of the Ig-like domain of HaSV VLPs:

The tetravirus Ig-like domain can be substituted for other structures without interfering with particle formation.

(i) Substitution with loop structures.

The purpose of this experiment was to show that the region encoding the Ig-like domain of tetravirus coat proteins could be exchanged for a minimum loop structure without affecting particle formation and RNA encapsidation. Such loops could be used to modify the host cell tropism of VLPs.

The HaSV p71 coat protein ORF was modified by removing the Ig-like domain between residues Q276-T416 and inserting a linker of five SGSGS residues (SEQ ID NO:11). This was done by the method of Imai et al. (1991) with the primers HR2noIgL (CTGCGGTAGGCTAGTCGGGGT) (SEQ ID NO:12) and HR2Loop (AGTGGAAGTGGCACTACTCGACCCTCCTCTCGTAG G), the latter having an anchor sequence encoding the SGSGS linker (SEQ ID NO:13). The PCR with kinased primers was performed on the plasmid pFBp71 which contained the p71 ORF and the ends of the resulting 6.8 kb fragment were ligated and transformed into E. coli and screened. The resulting plasmid pFBHloop was used to produce a recombinant baculovirus with the Bac-to-Bac system (Gibco-BRL). Particles were purified as for HaSV virions and showed the expected dimensions and morphology of 32–34 nM diameter and a smoother appearance than unmodified VLPs. The particles with modified p71 also encapsidated RNA as seen by the presence of RNA on a formaldehyde RNA gel after RNA extraction from the particles.

The Hloop construct can also be made by inserting an SGSGS (SEQ ID NO:11) loop domain at alternative sites of the tetravirus coat protein. For example, an SGSGS (SEQ ID NO:11) loop can be placed with a similar procedure to the above HR2loop, between G281 and E414. Or alternatively as an addition on one of the loops of the endogenous Ig-like domain itself; for example D353 and E358.

That loop structures are likely to give tetravirus VLPs predetermined host cell tropisms is evident in the comparison of the crystal structures of nodavirus and tetravirus coat proteins (Munshi et al., 1996). That is, at the analogous region of the Ig-like domain of the tetravirus coat protein, nodavirus coat protein have a pentapeptide loop with varying sequences (Dasgupta and Sgro, 1989). Hence replacement of the tetravirus Ig-like domain with the pentapeptide loop, ATTFA (SEQ ID NO:14), of the flock house virus (Wery et al., 1994) will likely give the resulting VLPs a binding and entry affinity to Drosophila cells similar to FHV. Another means of modifying the host cell tropism of tetravirus VLPs is to place the tripeptide sequence, RGD, in an accessible place on the coat protein. This will likely give the resulting VLPs binding affinity for RGD receptors of the integrin family of proteins located on many human cells (Pierschbacher and Ruoslahti, 1984). This can either be done with the nodavirus-like loop structure or by replacing an existing tripeptide sequence with RGD on one of the loops present on the endogenous tetravirus Ig-like domain.

Loop structures with binding affinities to cells with particular cell surface epitopes should be readily obtained with stochastic methods. One such method would be based on the pSKAN procedure (MoBiTec) which provides a 6–8 residue loop having desired binding affinities with a phagemid display system (Rottgen and Collins, 1995). A second method would be based on the use of the tetravirus coat protein itself to form VLPs with variable loop regions which are then selected for desired binding affinities. Recovery of VLPs with a desired affinity produced from this second method is facilitated by the fact that the VLPs will encapsidate the mRNA encoding the desirable loop region. A reiterative process will enrich for the VLPs with the desired affinity. This may be achieved by a process similar to the pSKAN procedure but suitably modified to account for the non-replicating nature of VLPs.

In detail, an altered loop version of the HaSV p71, pFBHLoop, may be used to place a hypervariable region, derived from a loop primer, in the loop region. The primer HR2noIgL (CTGCGGTAGGCTAGTCGGGGT) (SEQ ID NO:13) can then be used in conjunction with HR2LoopVar (NNNNNNNNNNNNNNNNCTCGACCCTCCTCTCGTAG G) (SEQ ID NO:15), to PCR a 6.8 kb fragment from pFBp71 which is then ligated to itself to produce a series of plasmids with p71 having different loop regions behind the polyhedrin promoter. These plasmids may then be used to produce pools of colonies with recombinant baculoviruses produced with the Bac-to-Bac system. Recombinant baculoviruses would then be prepared from the pools and used to transfect Sf9 cells. After 6 days, the Sf9 cells would be lysed with freeze-thaw and sonication (0.1% Triton X-100 in Tris buffer pH 8.0) and the particles allowed to mature by incubation a 4° C. for 1 week. The lysate can then be incubated with the desired ligand or surface epitope protein bound to magnetic beads according to the manufacturer (Dynal). The bound particles will be washed extensively but gently and directly extracted for RNA without elution. The RNA can then be used to perform RT-PCR with primers HR236F5 (AGAAGAAACCAACGGCGT) (SEQ ID NO:16) and HR2R2140 (AGGACGTTGCCTCCGACTTC) (SEQ ID NO:17) to produce a 1.7 kb fragment which can be digested with EcoRI and NotI enzymes then ligated to the larger fragment of pFBp71 resulting from digestion of the same two enzymes and having the rest of the HaSV p71 ORF. The resulting plasmid is then used to commence a reiterative second round of recombinant baculovirus production/transfection/particle binding/RT-PCR/plasmid preparation.

At least three rounds of recombinant baculovirus production/transfection/particle binding/RT-PCR/plasmid preparation would be required to arrive at particles with loops having affinity to the desired surface epitope.

(ii) Substitution with small proteins.

The purpose of this experiment was to demonstrate that small proteins with less than 30 kDa molecular weight can be inserted into the Ig-like domain of tetravirus coat proteins so that when VLPs are made the small protein is displayed on the outside of the particles. This can either be used to modify host cell tropism or to produce vaccines to the protein. For example, it was demonstrated that the 27 kDa green fluorescent protein (GFP) (Prasher et al., 1992) could be displayed on the outside of the NωV VLP. This was achieved by a procedure similar to that described in Example 4 to insert the HaSV Ig-like domain into the NωV coat protein. The procedure utilised the primers WGFPN (AGTACTCTTCGCAGAGTATGAGTAAAGGAGAAGA ACTT) (SEQ ID NO:18) and WGFPC (ATGACTCTTCGAGTACTGCCACTTCCACTTTTGTAT AGTTCATCCATG CC) (SEQ ID NO:19) to perform PCR on gfp10 cDNA (Prasher et al., 1992) to produce a 750 bp fragment which, when digested with Eam 1104I, had complementary ends to the Eam 1104I digested 6.4 kb PCR fragment produced with ω1 and ω2 from pFBWCAP. When ligated together into pFBWGFP, a hybrid NωV coat protein was formed having the primary structure: (NωV M1-Q280)-(GFP)-(linker peptide SGSGS)-(NωV T415-stop 445). This plasmid was used to produce a recombinant baculovirus according to the Bac-to-Bac system.

The hybrid protein was expressed in a manner similar to pFBWCAP and fluorescing cells were evident when irradiated with UV light. Particles were evident inside cells when examined with transmission electron microscopy (TEM), although they proved to be unstable when purified. However, when a particle was formed with a combination of proteins produced from pFBW loop virus and pFBWGFP virus at a ratio of 3:1, a stable VLP was formed which was able to be purified. Virus pFBW loop is the analogous NωV VLP version of Hloop having the loop structure and made by the same procedure and inserting the residues, SGSGS (SEQ ID NO:11) in place of the NωV Ig-like domain. The particle had a larger diameter, 45 nm, and the morphology showed larger protrusions on the outside of the purified particles. The particles were shown to encapsidate RNA.

The successful demonstration of hybrid tetravirus/GFP particles showed that proteins of less than 30 kDa could be displayed on the outside of the tetravirus particle. If such proteins possess binding affinities for cell surface proteins, then the tropism of the VLPs could be predetermined.

Immunoglobulin domains or lectins are excellent examples of such proteins which could be inserted into the region specified as the Ig-like domain of tetravirus coat proteins. However, certain modifications may be necessary to the proteins before their insertion to the tetravirus coat protein ORF. This is because of the need for the N-terminus and C-terminus to be adjacent in the tertiary structure of the protein as this conformation is evident in the tertiary structure of the tetravirus Ig-like domain. It is this conformation which makes the Ig-like domain exchange for other proteins possible without extensive reconstruction that would be detrimental to the conformation of the tetravirus coat protein. Examples of proteins to be modified to make the N- and C-termini adjacent are the V- and C-type domains of the Immunoglobulin superfamily and Ig-like domains from antibodies where the N-termini are separated from the C-termini by nearly the length of the protein (Bork et al., 1994, Williams and Barclay, 1988). Examination of the three dimensional structure of candidate proteins for insertion into tetravirus coat proteins will show if modifications are necessary. An example of how to modify proteins with Ig-like domains for insertion into tetravirus coat proteins is provided below.

(iii) Substitution with exogenous Ig-like domains.

The use of protein members of the Immunoglobulin superfamily is particularly desirable for determining tropisms for tetravirus VLPs as many of these proteins are known to be involved in cell surface recognition (Williams and Barclay, 1988), and in binding events such as those between antibodies and their respective antigens (Rees et al., 1994). This makes it likely that the presence of such proteins on the exterior surface of the tetravirus VLPs will cause the VLPs to bind to the same cells that are normally bound by the proteins.

However, most such Ig-like proteins have their N- and C-termini at the opposite ends of the three dimensional structure of the protein and thus modification of the Ig-like protein is necessary before insertion into the tetravirus coat protein as discussed in the previous section. Modification may be achieved by adding a 15–20 residue peptide linker which connects the last tetravirus coat protein residue before the commencement of the tetravirus Ig-like domain to the N-terminus of the nominated Ig-like domain to be inserted into the region of the tetravirus Ig-like domain. In such a manner the N-terminus, which would normally be at the non-proximal end of the Ig-like domain, is connected to the surface of the tetravirus capsid. The C-terminus of the nominated Ig-like domain is then connected to the residue terminating the tetravirus Ig-like domain by a shorter 3–5 residue peptide linker. Lengths of the linkers need to be empirically determined for optimal conformation of the Ig-like domain on the surface of the VLP. Composition of the peptide linkers may be alternating Ser-Gly residues for the required length as described by Bird et al. (1988).

Alternative linker compositions may be more optimal in some cases such as (Gly 4Ser) 4 (Somia et al., 1995). For example, the construction of one such hybrid tetravirus coat protein employing the NωV coat protein would be (NωV M1-Q280)-(linker peptide [SerGly]8)-(N-term-V-type Ig domain-C-term)-(linker peptide SerGlySer)-(NωV T415-stop 445).

An example of how a V-type Ig may be placed into the tetravirus coat protein so as to modify the tropism of the VLP to human cells having the low density lipoprotein receptor is based on the work of Somia et al. (1995). A 400 bp fragment containing the gamma Ig region of the C7 hybridoma is produced with PCR from pBS(Gly 4Ser) 4 Somia et al. (1995) with the primer GlySer (GGCGGTGGCGGATCGGGCGGT) (SEQ ID NO:20) and GammaC GCCTTTAATTAATGAGGAGAC) (SEQ ID NO:21) and blunt end cloned to the 6.8 kb PCR fragment from pFBp71 with the primers HR2noIgL (CTGCGGTAGGCTAGTCGGGGT) (SEQ ID NO:12) and HR2LoopIg (AGTGGCACTACTCGACCCTCCTCTCGTAGG) (SEQ ID NO:22), the latter having an anchor sequence encoding a SGS linker. The resulting plasmid produces a protein having the primary structure (HaSV p71 M1-Q276)-(Gly 4Ser) 4-(gamma V-type Ig domain)-(SerGlySer)-(HaSV p71 T421-N446) when used to produce a recombinant baculovirus with the Bac-to-Bac system. Stable VLPs encapsidating RNA and capable of binding to QT6 cells, should be produced when this protein is expressed (Somia et al., 1995). Suitable Ig-like domains with binding specificities for desired cell types can also be derived stochastically with phage display techniques (Clackson et al., 1991).

EXAMPLE 6

Production of HaSV VLPs with low reactivity to the vertebrate immune system:

VLPs produced from tetravirus coat proteins can be made to have a low reactivity to the vertebrate immune system.

The human immune system is one of the largest obstacles to therapeutics based on particles containing nucleic acids. This limits their use to only a few occasions before an immune reaction neutralises the particles before they enter cells. However, hybrid tetravirus VLPs may have a means to counter this phenomenon by being "invisible" to the immune system. Experiments described below show that >98% of the VLPs immunogenicity to the rabbit and mouse immune systems resides in the tetravirus Ig-like domain and that the VLP's contiguous surface (ie. the surface created by loop-type constructs of the tetravirus coat protein) displays little, if any, immunogenicity in the presence of an Ig-like feature on the surface. This suggests that the placement of an Ig-like domain from a human source will not induce the human immune system conditioned to the presence of such proteins (i.e. similar to a blood transfusion with different human antibodies with human Ig-like domains).

To determine the region of the tetravirus coat protein responsible for immunogenicity of the particle, the following experiment was conducted. Plasmid pT7T2p69 was constructed as outlined by Hanzlik et al. (1995) for plasmid pT7T2p71. However, instead of expressing HaSV p71 in bacteria as for pT7T2p71, the plasmid pT7T2p69 expressed a fusion of a part of HaSV p17 (Hanzlik et al., 1995) and the p71 coat protein by virtue of a frame-shift mutation after nucleotide C569 where an additional C was inserted. Thus fusion protein produced incorporated M1-P96 of p17 and N70-N646 of p71. The region encoding the Ig-like domain of p71 was deleted using the method of Imai et al. (1991) using pFBp71 and the primers HR2noIgR and HR2noIgL (see above for sequences). This removed residues Q280-T415 from the resulting protein expressed by the recombinant baculovirus produced from the plasmid with the Bac-to-Bac system. When Western blotted on two different membranes and separately probed with anti-p17 or anti-p71 antisera (Hanzlik et al., 1995) and detected using alkaline phosphatase induced luminescence on film, the signal from the deleted protein probed with anti-p71 was less than 2% than that of the non-deleted protein. Normalisation of the anti-p17 signal which accounted for differing amounts of antigen on the membrane was achieved with the signal from p17 which was unaffected by the deletion. The phenomenon of the Ig-like domain accounting for >98% of the immunogenicity was true for two different rabbit and three different mouse polyclonal antiseras. This observation is supported by that of Hanzlik et al. (1995) who noted that the anti-seras against NωV and HaSV did not cross react despite >80% identity in areas of the coat protein other than the Ig-like domain which had <35% identity.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Agrawal, D. K. and Johnson, J. E. (1992). Virology 190, 89–97

Agrawal, D. K. and Johnson, J. E. (1995). Virology 207, 89–97.

Bird, R. E. and Walker, B. W. (1988) TibTech 9, 132–137.

Bork, P., Holm, L., and Sander, C. (1994) J. Mol. Biol. 242, 309–320

Bravo, A., Hendrick, K. Jansens, S. and Peferaen, M. (1992). J. of Invert. Pathol. 60, 247–253.

Clackson, T., Hoogenboom, H. R., Griffiths, A. D. and Winter, G. (1991) Nature 352, 624–628

Dasgupta, R. and Sgro, J-Y. (1989) Nuc. Acids Res. 17, 7525–7526.

Hanzlik and Gordon, (1997) Advances in Virus Research (in press)

Hanzlik, T. N., Dorrian, S. J., Gordon, K. H. J. and Christian, P. D. (1993). J. Gen. Virol. 74, 1105–1110.

Hanzlik, T. N., Dorrian, S. J., Johnson, K. N., Brooks, E. M. and Gordon, K. H. J. (1995). J. Gen. Virol. 76, 799–811.

Hughes, P. R. and Wood, H. A. (1981) J. Invert. Pathol. 37, 154–159.

Hussey, R. E., Richardson, N. E., Kowalski, M., Brown, N. R., Chang, H.-C., Siliciano, R. F., Dorfman, T., Walker, B., Sodroski, J. & Reinherz, E. L. (1988). Nature 331, 78–81.

Imai, Y., Matsushima, Y. Sugimura, T., and Terada, M. (1991) Nuc. Acids Res. 19, 2785.

Jefferson, R. A., Burgess, S. M. and Hirsh, D. (1986) Proc. Natl. Acad. Sci USA 86, 8447–8451.

Lentz (1990) J. Gen. Virol. 71, 751–766.

Munshi, S., Liljas, L., Cavarelli, J., Bomu, W., McKinney, B., Reddy, V. and Johnson, J. E. (1996). J. Mol. Biol. 261, 1–10.

Padgett, K. A. and Sorge, J. A. (1996) Gene 168, 31–35.

Prasher, D. C., Eckenrode, V. K. Ward, W. W., Prendergast, F. G. and Cormier, M. J. (1992) Gene 141, 229–233

Pierschbacher, M. D. and Ruoslahti, E. (1984) Nature 309, 30–33.

Rees, A. R., Staunton, D., Webster, D. M., Searle, S. J., Henry, A. H., Pedersen, J. T. (1994) TibTech 12, 199–206.

Rottgen, P., and Collins, J. (1995) Gene 164, 243–250.

Sakihama, T., Smolyar, A. & Reinherz, E. L. (1995a). Proc. Natl. Acad. Sci. USA 92, 6444–6448.

Sakihama, T., Smolyar, A. & Reinherz, E. L. (1995b). Immunology Today 16, 581–587.

Somia, N. V., Zoppe, M., Verma, I. M. (1995) Proc. Natl. Acad. Sci. USA 92, 7570–7574

Weber, S. & Karjalainen, K. (1993). Int. Immunol. 5, 695–698.

Williams, A. F. and Barclay, A. N. (1988) Ann. Rev. Immunol. 6, 381–405

Yusibov, V. Kumar, A. North, A. Johnson, J. E. and Loesch-Fries, S. (1996) J. Gen Virol. 77, 567–573.

What is claimed is:

1. An isolated small RNA virus selected from Picornaviridae, Nodaviridae and Tetraviridae which includes an Ig-like domain within the wild-type coat protein(s), wherein said Ig-like domain has been altered or substituted so as to modify host cell tropism.

2. The isolated virus of claim 1, wherein the Ig-like domain has been altered such that the virus selectively binds and infects a predetermined cell type which is other than the virus' normal host cell type(s).

3. The isolated virus of claim 2, wherein the predetermined cell type is a cell type belonging to an insect species outside of the virus' normal host species range.

4. The isolated virus of claim 1, wherein the virus is Tetraviridae.

5. The isolated virus of claim 4, wherein the virus is a member of the Nudaurelia β-like or Nudaurelia ω-like virus families.

6. The isolated virus of claim 5, wherein the virus is selected from *Helicoverpa armigera* stunt virus (HaSV), *Nudaurelia ω virus* (NωV) and Nudaurelia β virus (NβV).

7. The isolated virus of claim 1, wherein said Ig-like domain is altered or substituted by including an Ig-like domain from an exogenous protein.

8. The isolated virus of claim 7, wherein the Ig-like domain derived from an exogenous protein is selected from variable (V) or constant (C) domains of antibodies, and Ig-like domains of cell adhesion proteins and receptors.

9. The isolated virus of claim 1, wherein the Ig-like domain is altered or substituted by including a non-Ig-like tertiary structure.

10. The isolated virus of claim 9, wherein the non-Ig-like tertiary structure is selected from peptide loops, proteins of <30 kDa and lectins.

11. The isolated virus of claim 9, wherein the non-Ig-like tertiary structure is antigenic.

12. A virus-like particle (VLP) prepared from expression of a coat protein gene(s) derived from a small RNA virus selected from Picornaviridae, Nodaviridae and Tetraviridae which includes an Ig-like domain within the wild-type coat protein(s), said gene(s) having been altered such that the Ig-like domain of the expressed coat protein is altered or substituted so as to modify host cell tropism.

13. The VLP of claim 12, wherein the Ig-like domain has been altered such that the virus selectively binds and infects a predetermined cell type which is other than a host cell type(s) which the VLP, absent the alteration or substitution of the Ig-like domain, would otherwise bind and infect.

14. The VLP of claim 13, wherein the predetermined cell type is a cell type belonging to an insect species.

15. The VLP of claim 12, wherein the virus from which the coat protein gene(s) is derived is selected from Tetraviridae.

16. The VLP of claim 15, wherein the virus is a member of the Nudaurelia β-like or Nudaurelia ω-like virus families.

17. The VLP of claim 16, wherein the virus is selected from *Helicoverpa armigera* stunt virus (HaSV), Nudaurelia ω virus (NωV) and Nudaurelia β virus (NβV).

18. The VLP of claim 12, wherein said Ig-like domain is altered or substituted by including an Ig-like domain from an exogenous protein.

19. The VLP of claim 18, wherein the Ig-like domain derived from an exogenous protein is selected from variable (V) or constant (C) domains of antibodies, and Ig-like domains of cell adhesion proteins and receptors.

20. The VLP according to claim 12, wherein the Ig-like domain is altered or substituted by including a non-Ig-like tertiary structure.

21. The VLP of claim 20, wherein the non-Ig-like tertiary structure is selected from peptide loops, proteins of <30 kDa and lectins.

22. The VLP of claim 20, wherein the non-Ig-like tertiary structure is antigenic.

23. The VLP according to claim 12, further comprising an exogenous nucleic acid molecule, wherein said exogenous nucleic acid molecule is encapsidated within the VLP and is expressed when said VLP binds and infects a host cell.

24. The VLP of claim 23, wherein the exogenous nucleic acid molecule is insecticidal or encodes an insecticidal toxin.

25. The VLP of claim 23, wherein the exogenous nucleic acid molecule encodes a cytotoxin.

26. A virus-like particle (VLP) prepared from expression of a coat protein gene(s) from a small RNA virus selected from Picornaviridae, Nodaviridae and Tetraviridae, which includes an Ig-like domain within the wild-type coat protein(s), said gene(s) having been altered such that the Ig-like domain of the expressed coat protein(s) is altered or substituted so that the VLP presents a surface located antigen to elicit an immune response in a host organism.

27. The VLP of claim 26, wherein the small RNA virus is selected from Tetraviridae.

28. The VLP of claim 27, wherein the virus is a member of the Nudaurelia β-like or Nudaurelia ω-like virus families.

29. The VLP of claim 28, wherein the virus is selected from *Helicoverpa armigera* stunt virus (HaSV), Nudaurelia ω virus (NωV) and Nudaurelia β virus (NβV).

30. The VLP of claim 26, wherein the Ig-like domain is altered or substituted by including a non-Ig-like tertiary structure.

31. The VLP of claim 30, wherein the non-Ig-like tertiary structure is selected from peptide loops, proteins of <30 kDa and lectins.

32. The VLP of claim 13, further comprising an exogenous nucleic acid molecule, wherein said exogenous nucleic acid molecule is encapsidated within the VLP and is expressed when said VLP binds and infects a host cell.

33. The VLP of claim 32, wherein the exogenous nucleic acid molecule is insecticidal or encodes an insecticidal toxin.

34. The VLP of claim 33, wherein said predetermined cell type is a midgut goblet cell.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
    (A) LENGTH: 2478 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:1:

```
GTTTTTCTTT CTTTACCAAG TGTGGTAAAA TTTAAACAAA GAAGAAAACC AGGACCGTAA    60
CCCGGCCCTT ACACACCTCG AGTCCGTGAC CACCGGATTA TACGTCGCCC ACCACACGGC   120
GCCTTTTCCG ACCACTCTCG AGAGTCGTTG GGAGTTTCGT CCGTGACCAC CCGGTTGGCA   180
GTCGACAGAC GCTTCCGGAC CACTAGAACC TCCTCGAGCG ACGCACACAC AGCACACACA   240
CCGCCTTAGC TGCACCTACG GCAGCGTTGA TAGCGCGGAT TTATGAGCGA GCACACCATC   300
GCCCACTCCA TCACATTACC ACCCGGTTAC ACCCTTGCCC TAATACCCCC TGAACCTGAA   360
GCAGGATGGG AGATGCTGGA GTGGCGTCAC AGCGACCTCA CAACCGTCGC GGAACCCGTA   420
ACGTTCGGGT CAGCGCCAAC ACCGTCACCG TCAATGGTAG AAGAAACCAA CGGCGTCGGA   480
CCGGAAGGCA AGTTTCTCCC CCTGACAATT TCACCGCTGC TGCACAAGAC CTCGCGCAAA   540
GCCTTGACGC CAACACCGTC ACTTTCCCCG CTAACATCTC TAGCATGCCC GAATTCCGGA   600
ATTGGGCCAA GGGAAAGATC GACCTCGACT CCGATTCCAT CGGCTGGTAC TTCAAGTACC   660
TTGACCCAGC GGGTGCTACA GAGTCTGCGC GCGCCGTCGG CGAGTACTCG AAGATCCCTG   720
ACGGCCTCGT CAAGTTCTCC GTCGACGCAG AGATAAGAGA GATCTATAAC GAGGAGTGCC   780
CCGTCGTCAC TGACGTGTCC GTCCCCCTCG ACGGCCGCCA GTGGAGCCTC TCGATTTTCT   840
CCTTTCCGAT GTTCAGAACC GCCTACGTCG CCGTAGCGAA CGTCGAGAAC AAGGAGATGT   900
CGCTCGACGT TGTCAACGAC CTCATCGAGT GGCTCAACAA TCTCGCCGAC TGGCGTTATG   960
TCGTTGACTC TGAACAGTGG ATTAACTTCA CCAATGACAC CACGTACTAC GTCCGCATCC  1020
GCGTTCTACG TCCAACCTAC GACGTTCCAG ACCCCACAGA GGGCCTTGTT CGCACAGTCT  1080
CAGACTACCG CCTCACTTAT AAGGCGATAA CATGTGAAGC CAACATGCCA ACACTCGTCG  1140
ACCAAGGCTT TTGGATCGGC GGCCAGTACG CTCTCACCCC GACTAGCCTA CCGCAGTACG  1200
ACGTCAGCGA GGCCTACGCT CTGCACACTT TGACCTTCGC CAGACCATCC AGCGCCGCTG  1260
CACTCGCGTT TGTGTGGGCA GGTTTGCCAC AGGGTGGCAC TGCGCCTGCA GGCACTCCAG  1320
CCTGGGAGCA GGCATCCTCG GGTGGCTACC TCACCTGGCG CCACAACGGT ACTACTTTCC  1380
CAGCTGGCTC CGTTAGCTAC GTTCTCCCTG AGGGTTTCGC CCTTGAGCGC TACGACCCGA  1440
ACGACGGCTC TTGGACCGAC TTCGCTTCCG CAGGAGACAC CGTCACTTTC CGGCAGGTCG  1500
CCGTCGACGA GGTCGTTGTG ACCAACAACC CCGCCGGCGG CGGCAGCGCC CCCACCTTCA  1560
CCGTGAGAGT GCCCCCTTCA AACGCTTACA CCAACACCGT GTTTAGGAAC ACGCTCTTAG  1620
AGACTCGACC CTCCTCTCGT AGGCTCGAAC TCCCTATGCC ACCTGCTGAC TTTGGACAGA  1680
CGGTCGCCAA CAACCCGAAG ATCGAGCAGT CGCTTCTTAA AGAAACACTT GGCTGCTATT  1740
TGGTCCACTC CAAAATGCGA AACCCCGTTT TCCAGCTCAC GCCAGCCAGC TCCTTTGGCG  1800
CCGTTTCCTT CAACAATCCG GGTTATGAGC GCACACGCGA CCTCCCGGAC TACACTGGCA  1860
TCCGTGACTC ATTCGACCAG AACATGTCCA CCGCTGTGGC CCACTTCCGC TCACTCTCCC  1920
ACTCCTGCAG TATCGTCACT AAGACCTACC AGGGTTGGGA AGGCGTCACG AACGTCAACA  1980
CGCCTTTCGG CCAATTCGCG CACGCGGGCC TCCTCAAGAA TGAGGAGATC CTCTGCCTCG  2040
```

```
CCGACGACCT GGCCACCCGT CTCACAGGTG TCTACCCCGC CACTGACAAC TTCGCGGCCG      2100

CCGTTTCTGC CTTCGCCGCG AACATGCTGT CCTCCGTGCT GAAGTCGGAG GCAACGTCCT      2160

CCATCATCAA GTCCGTTGGC GAGACTGCCG TCGGCGCGGC TCAGTCCGGC CTCGCGAAGC      2220

TACCCGGACT GCTAATGAGT GTACCAGGGA AGATTGCCGC GCGTGTCCGC GCGCGCCGAG      2280

CGCGCCGCCG CGCCGCTCGT GCCAATTAGT TTGCTCGCTC CTGTTTCGCC GTTTCGTAAA      2340

ACGGCGTGGT CCCGCACATT ACGCGTACCC TAAAGACTCT GGTGAGTCCC CGTCGTTACA      2400

CGACGGGTCT GCCGCGGTTC GATTCCATTC CCAAGCGGCA AGAAGGACGT AGTTAGCTCT      2460

GCGTCCCTCG GGATACCA                                                   2478
```

(2) INFORMATION FOR SEQ ID NO:2:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ser Glu His Thr Ile Ala His Ser Ile Thr Leu Pro Pro Gly Tyr
 1               5                  10                  15

Thr Leu Ala Leu Ile Pro Pro Glu Pro Glu Ala Gly Trp Glu Met Leu
            20                  25                  30

Glu Trp Arg His Ser Asp Leu Thr Thr Val Ala Glu Pro Val Thr Phe
        35                  40                  45

Gly Ser Ala Pro Thr Pro Ser Pro Ser Met Val Glu Glu Thr Asn Gly
 50                  55                  60

Val Gly Pro Glu Gly Lys Phe Leu Pro Leu Thr Ile Ser Pro Leu Leu
65                  70                  75                  80

His Lys Thr Ser Arg Lys Ala Leu Thr Pro Thr Pro Ser Leu Ser Pro
            85                  90                  95

Leu Thr Ser Leu Ala Cys Pro Asn Ser Gly Ile Gly Pro Arg Glu Arg
           100                 105                 110

Ser Thr Ser Thr Pro Ile Pro Ser Ala Gly Thr Ser Ser Thr Leu Thr
        115                 120                 125

Gln Arg Val Leu Gln Ser Leu Arg Ala Pro Ser Ala Ser Thr Arg Arg
    130                 135                 140

Ser Leu Thr Ala Ser Ser Ser Pro Ser Thr Gln Arg
145                 150                 155
```

(2) INFORMATION FOR SEQ ID NO:3:

(i) SEQUENCE CHARACTERISTICS:
        (A) LENGTH: 647 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Gly Asp Ala Gly Val Ala Ser Gln Arg Pro His Asn Arg Arg Gly
 1               5                  10                  15

Thr Arg Asn Val Arg Val Ser Ala Asn Thr Val Thr Val Asn Gly Arg
            20                  25                  30

Arg Asn Gln Arg Arg Arg Thr Gly Arg Gln Val Ser Pro Pro Asp Asn
```

-continued

```
            35                  40                  45
Phe Thr Ala Ala Ala Gln Asp Leu Ala Gln Ser Leu Asp Ala Asn Thr
        50                  55                  60

Val Thr Phe Pro Ala Asn Ile Ser Ser Met Pro Glu Phe Arg Asn Trp
 65                  70                  75                  80

Ala Lys Gly Lys Ile Asp Leu Asp Ser Asp Ser Ile Gly Trp Tyr Phe
                 85                  90                  95

Lys Tyr Leu Asp Pro Ala Gly Ala Thr Glu Ser Ala Arg Ala Val Gly
                100                 105                 110

Glu Tyr Ser Lys Ile Pro Asp Gly Leu Val Lys Phe Ser Val Asp Ala
            115                 120                 125

Glu Ile Arg Glu Ile Tyr Asn Glu Glu Cys Pro Val Val Thr Asp Val
        130                 135                 140

Ser Val Pro Leu Asp Gly Arg Gln Trp Ser Leu Ser Ile Phe Ser Phe
145                 150                 155                 160

Pro Met Phe Arg Thr Ala Tyr Val Ala Val Ala Asn Val Glu Asn Lys
                165                 170                 175

Glu Met Ser Leu Asp Val Val Asn Asp Leu Ile Glu Trp Leu Asn Asn
            180                 185                 190

Leu Ala Asp Trp Arg Tyr Val Val Asp Ser Glu Gln Trp Ile Asn Phe
        195                 200                 205

Thr Asn Asp Thr Thr Tyr Tyr Val Arg Ile Arg Val Leu Arg Pro Thr
    210                 215                 220

Tyr Asp Val Pro Asp Pro Thr Glu Gly Leu Val Arg Thr Val Ser Asp
225                 230                 235                 240

Tyr Arg Leu Thr Tyr Lys Ala Ile Thr Cys Glu Ala Asn Met Pro Thr
                245                 250                 255

Leu Val Asp Gln Gly Phe Trp Ile Gly Gly Gln Tyr Ala Leu Thr Pro
            260                 265                 270

Thr Ser Leu Pro Gln Tyr Asp Val Ser Glu Ala Tyr Ala Leu His Thr
        275                 280                 285

Leu Thr Phe Ala Arg Pro Ser Ala Ala Ala Leu Ala Phe Val Trp
    290                 295                 300

Ala Gly Leu Pro Gln Gly Gly Thr Ala Pro Ala Gly Thr Pro Ala Trp
305                 310                 315                 320

Glu Gln Ala Ser Ser Gly Gly Tyr Leu Thr Trp Arg His Asn Gly Thr
                325                 330                 335

Thr Phe Pro Ala Gly Ser Val Ser Tyr Val Leu Pro Glu Gly Phe Ala
            340                 345                 350

Leu Glu Arg Tyr Asp Pro Asn Asp Gly Ser Trp Thr Asp Phe Ala Ser
        355                 360                 365

Ala Gly Asp Thr Val Thr Phe Arg Gln Val Ala Val Asp Glu Val Val
    370                 375                 380

Val Thr Asn Asn Pro Ala Gly Gly Ser Ala Pro Thr Phe Thr Val
385                 390                 395                 400

Arg Val Pro Pro Ser Asn Ala Tyr Thr Asn Thr Val Phe Arg Asn Thr
                405                 410                 415

Leu Leu Glu Thr Arg Pro Ser Ser Arg Arg Leu Glu Leu Pro Met Pro
            420                 425                 430

Pro Ala Asp Phe Gly Gln Thr Val Ala Asn Asn Pro Lys Ile Glu Gln
        435                 440                 445

Ser Leu Leu Lys Glu Thr Leu Gly Cys Tyr Leu Val His Ser Lys Met
    450                 455                 460
```

```
Arg Asn Pro Val Phe Gln Leu Thr Pro Ala Ser Ser Phe Gly Ala Val
465                 470                 475                 480

Ser Phe Asn Asn Pro Gly Tyr Glu Arg Thr Arg Asp Leu Pro Asp Tyr
                485                 490                 495

Thr Gly Ile Arg Asp Ser Phe Asp Gln Asn Met Ser Thr Ala Val Ala
            500                 505                 510

His Phe Arg Ser Leu Ser His Ser Cys Ser Ile Val Thr Lys Thr Tyr
            515                 520                 525

Gln Gly Trp Glu Gly Val Thr Asn Val Asn Thr Pro Phe Gly Gln Phe
        530                 535                 540

Ala His Ala Gly Leu Leu Lys Asn Glu Glu Ile Leu Cys Leu Ala Asp
545                 550                 555                 560

Asp Leu Ala Thr Arg Leu Thr Gly Val Tyr Pro Ala Thr Asp Asn Phe
                565                 570                 575

Ala Ala Ala Val Ser Ala Phe Ala Ala Asn Met Leu Ser Ser Val Leu
                580                 585                 590

Lys Ser Glu Ala Thr Ser Ser Ile Ile Lys Ser Val Gly Glu Thr Ala
            595                 600                 605

Val Gly Ala Ala Gln Ser Gly Leu Ala Lys Leu Pro Gly Leu Leu Met
        610                 615                 620

Ser Val Pro Gly Lys Ile Ala Ala Arg Val Arg Ala Arg Arg Ala Arg
625                 630                 635                 640

Arg Arg Ala Ala Arg Ala Asn
                645

(2) INFORMATION FOR SEQ ID NO:4:

(i) SEQUENCE CHARACTERISTICS:
        (A) LENGTH: 6534 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

CCTTGATATC GCTTGTGTTA GGCACAAGTG ATGAAGACG CAAGCAAGCA GCTCCGCGTC      60

CTGGATGCCC AGGAGCGCGC GAAGGCCGCC TTCCAACTCG ACTTCATAGC CTCTGTCGAG    120

ACTTTGGAAG ACGCTCAGGA GAAGTACGAG GGCATGATGT TCGCAGTGG CACGAAACTG    180

CCATCAACCC ATATTAAGTT GGCAATCGAT CTGAGAGTTG CGGAGAAAGA TCTACGCCGG    240

CACGTTAAGA ATGTACCGAC AGTGCTGGAA ATTGGACCCA GTGTTGAGAG CGTGCGTTAC    300

GCTGTGCAGA CTCGAGACAA GGAGAGAGTC CATGGCTGCA CCTTCTCCGA CGCGCGTGAT    360

AACCTCCGCC ACAATAAGAT CGGTTATGAA GCCCATTACG ACAGAAAGAT TGGACCTGAC    420

GCCGCCCTTC TGGCCGCTGG TATCCCAACT GACACCTTCT GTGTCGACGG CTTCTCCAAT    480

GCGAGTACCA ATCCCCCCTC GCCATTGCCT GCCACTCACT TTACCCCGAT GGGGAAAGTA    540

ATAGTATTAT GGACGTGGCT AAAGGCATGG CTCTCCACGG CACCCACGTG ATATATGCGT    600

GGATGCATCT GCCCGTGGAA CTGCTAACGC TCACCGATGC AGACAATATT TTTGAAGGGT    660

TGACCCAGCG GGTGCTACAG AGTCTGCGCG CGCCGTCGGC GAGTACTCGA AGATCCCTGT    720

TCTCCGGTTA TAACGATTTT GGTTCGGCCT ATGTGCACGA TGCCCACCAT TGGGCTGGTT    780

GGCTTAAGCA TCGGGGAGTA GACACCCCGT ATGGCTTCTC CATATTGATC GACATACAAC    840

AGAGGTTCGG TATGCACACG AAATTAAAGA TCACCCGTGG GCACAGCAGT GGCAGTATCA    900
```

-continued

```
CCACCGTGTT CCCGTTGTCG AAATTGGGCT TGATCTGGGT GCCGAACATA GTCAAAATAA    960
TGTACCCTAA AGCCAAACAC GAGCCGGAGT ACATCGTCAC GGATAAGAAG AAGTATGAAG   1020
GCGTTTGCGT GTACGTCGGA ACGAGGGTGC AAAGTTCCGG CAAGTCTATT ACGCTCGCTG   1080
AGATTGTTCA ATACATCCGA ACAAGATTAA CACGCATCAT TCTGAATGGC ACTGTCCACG   1140
AGAAAACGTG GACCATAGCA GAGCAAGACA TTGAGCGACT TGCCGTTAGC ATTATGTTCC   1200
GCAAGAATGT GGAACGCGCT GTGTCTGAAA AGGCACTGAT GAGAGCGCAG AAGAAGTGCA   1260
AGAGCGCTGA AAAACAAGCG CTGCTGCCAG TTTGGATGCG GAGGATCGCC AATTGGTTCC   1320
AAGACAAATT TCAAATCGAC GAGGAGGTCG TACGCAAGCG CTACCTTGAG TGTCTCAAGG   1380
CGCAACCCTG GATCCACGCC GATAAAGTGG TGAACTGCGA GACCAAGCGC TATAACCCTA   1440
CTGTCGCCGA GGTGGGTCCT AAGAATCATT TGCTCGCCAC TACCGGATTG CGCGAGCTCC   1500
AAAGGGAAAT ACCCAGTGCT AACGAACCGC AAGATAGAGG AGCCAAGGCA TGGCACTCCG   1560
CTCACGCCGA TCTCGACATT TACGCCGAGG GACTCCGACT CGACTCCGCT AAAGAGGCAA   1620
GACTCGACCC TCCTCTCGTA GGCTCGAACT CCCTATGCCA CCTGCTGACT TTGGACAGAA   1680
CCAAGTGCGA GGGGTGCAAC AACATTGAAA TCGAGTACTG GACCGGACCC CCCGGTTCCG   1740
GGAAATCCAG GGCCGCTAAG CCGAGATTTG CAGATTTGCA GGGGGGCGTG TTGTACTGCG   1800
CCCCTACGCG CACGCTGCGC GACGCCCTCG ACGAAAGCGT CGTGCACCCT TCCCGTGTTT   1860
GCACTTACCA CAACGCACTG CATGTCGCTG CCAAAGAGTC TGGCAATAGG CCTTTTGACG   1920
TTATCGTCAT CGATGAAGCG GAGACGACGC CGGCTTGCTA CGTAGGTACG ATGCATCATG   1980
CATCGCCTAG TAGTAGGATC GTCTGTCTGG GCGATCCGCA CCAGATCGGT TACATCGACT   2040
TTTCGGATCG AAAAGACGAT TTGAAACCTT TCAGTATCAT AGCAGCCGAA TGTCGCACTC   2100
GTAGGTTTAA CACCACTTAT AGGTGCCCAC AAGACGTTTT AAACTTGCCC ATATTCAAAA   2160
CTCTATACCC GGACGCGATA TCGTTCAGCA ACAATTGAC TAGCATCCGT TACCTCACAC   2220
GGGCAAGATC AGTTACCCGA ACACGCCACG CTCAGACCCT GACGCAGGAC CAAAAGCCAC   2280
ATTCGGAACC GCCAGTGACC GCGCATGAGC CGCAGGCACG ACGTACGGAC GTTATAGTGC   2340
ATTACGCCGG CACTTTACCC GAAAGGGCAC TGTTAGAGAA GGTGCGGCAT ATAAACGTCG   2400
CGTTGACTCG GCACACAAAC GCCCTATATA TCAGGGACGA AAGTGAAAAA GGAGAGTTGG   2460
TACCTTCATT AATGACACCG CCAAGCTGGA GCACTTATCG GTGCACCCCC GTTGACAAGC   2520
AAATGGTACC GGATCCGGTT GCAGTGGAGC GAGAGAACGG ATCGTCTGGT CCGTGTGACT   2580
CCCACCATAT CGGCGCGATT ACTATATTGC AAGAGCTCGG CAAATTAACG GATACGAAAG   2640
GCGTACGAGT ATTTGAATCC GAAGCCGTCC CAACCGCTCA CCGGCGCGTA GTGCTTGACG   2700
GCAACCTCGA TTCAGGGCCC GATCGTTACC CGATGTATCA GTTCACTAAC CTCCGCGGGA   2760
CCAAATACAC GAATATCAAG GACAACCAAC AAGCGTTGCA TACGCTCGTC GGCCGGTATG   2820
CACGCAAGAT AAACAGCTCG AGCCGAGAGA CGCCGAGTTT GACGTTAAGA GAATCACAGC   2880
CAGCTCAAGA ATGGATTCCT TTTAGACACG CAGAGCCCGA GCAAGTCGAC AGTTGCTTTG   2940
CGACGCCATG CAAAAGATGC GAACGCGGCC ATGGCGTCGA TGACATCGAG GACTTCTGGT   3000
CGAACGAAGG CCAAAGAATT TCTTACCACC TTAAGGGCCA GCAAAAAGTC ATGGACCCCA   3060
CCAAACTGAA ACTTGGACAA GGTATCTCCG CGCATGAAAA ATGCGCTAAC ATTGCCTCAG   3120
CGCGTGGGTG AGGATTATCC AAGATACAGAT GAGCACGTCA GAGAAGTTCA TCTTCGCGAA   3180
TGGGCAGTCA GACCGCGATA CCATGTCTAT CATTGAGGCA CGCCTGCAGG AGAAGGCGCG   3240
```

```
GGAATTCAAA TCTATAGATA TCAAGGAGTT CGATACGGTA CATAACTGGG TCAGTATTCT    3300

TGTCTTCTCG TGGCGTTGCG ACCGTGGGTG CCCAGAGCAC CTTATCGAGT ATTTCGAGAA    3360

ACGCTCGAAA AGCCGGACGC TCTCAAGCCG CATAGGAAGC GTCGACGTTA GCTTCATGCT    3420

CGATTCTGGC GCTGTCTGGA CCATTGCCAG AAACACCTTA TTTGCCTCGG GTCTTATGCT    3480

CGCCCTTTTC GTCGGCGTCG ATTTCATCGC GGCGAAAGGC GATGATGTCT TCCTCGCAGG    3540

GAATAATTTG TACTTGGACG CAGAACGGCT TCGCATGGGA TCTTACTTAG CCGCAAACAA    3600

CTTGAAGATC GAGAAGACGG CGGTCGTGAG CTTTATAGGG TTTATCGTTT CCCAAGCCGC    3660

CGTCACAGCT GATGTCGTGC GTCTAGCCAC CCGGACTTAC GGTCGAAGTT ATAAAAACGT    3720

GATGATCTAG CGAGTATAAG ATAGCTATCG CTGACCACTG CAGTTGTTTA GATCACCGAG    3780

AACTCGTCTC ATGACCGCGA TCAACTGCGC CACCCTTTAC GGCACCTCGA AAGGTGCATC    3840

AATTATCTGA TGGACGCGTT GGACGATTCG GACACACTAA AATGAGCGAC CTACACTTGG    3900

ATCCCGGTTT TGTCATGCGG GTCACCCCCA TGAAGGTGGA CGAGCGGGTT TATTCCGGAC    3960

AAGATGGATG CCAACGTGCA GATAAGACCG GCGAGAAACA ACCCGAACCC AGGGCAACCA    4020

GGGCCGCGCA AACAACAACA ACAACGTCGA CGCAGGAGGC GGGGTCTAAA ACTTCCCCCC    4080

GTAGTCGCAC CGATTACCAG CCCGCCAGAT GGCCGAACCC CGAACCACGC GAACACCCGG    4140

GTCAACCGCG GTCGGACACG CGTGAGGGGG CTAAGGCAAG CGATGATGGA GAGTCCCATG    4200

GCAGCGACAT CAAGGCATGG ATTCACGACT ATCTAGACCC GGACGGAGAA TACAAGACGA    4260

GCCTGGACGA CGGGAAAATT CCCGACGGCG CGATACCTCA GTCAACATGC GGTCAATTTC    4320

GAGGGACCGT GGGCGCCAGA TACCCGGGAC TGAATTCTAC GACGCTACCG CTGGATGGCG    4380

GGACCTGGCC TCTACTAGTG ATGCATCTCC CGTTCTTCAG GCATCCGTTG TTGTTCATCA    4440

CCACCACCAG CAACACGGAA GTCGAAGTGA CGAACGCCGA TCTGGATGCG TTCGCGAACG    4500

ATTGGAACAA CAGGACGGAC TGGACCGAAG CGACGTACCC AAGTTGGGCG CAAGTCGGGA    4560

ACGTGTTTTA CATGGTCGTC CCGACCGAAG CGCTGACGGA CGTACCACCC CCGACTCAAC    4620

TGGGTGTATC AGGGTTACTC GAGAGTTACC GTCTGACATC GAGCGGCGTC ACAGCGTACT    4680

TCAACGCACC CACTCTCGTG AATCAGGGAG TGGCGGTGAT CGCGCAGTTC AACCGGACA    4740

AAGAACACCA GAAGGAGAAC CCGGACATAG TAGCCGGGAC CACCCAAACG GGCGGAACGT    4800

TACAGCTCGG CGGTTCAGGG CCGAACTACA CATTGACGAT GACGATCGGG GACCAGGTCG    4860

AGTTCGGGGG CGCAGCAATC CCGCTACCCA CGGTGTCGAT GGGGCCGATG CCGGAGTCGG    4920

GGCAGCTGGT GTTCCAGACT GCGAACCTGA CATTCGACGT CGGAAACACA ATCACCATCA    4980

CGACCACGCT GCCACCAGGG TCGGTGACGG GAATGTGGCA ATTCACAGCC AGCAACGGGA    5040

CGGACACCGT GACCGTGGAC GCGGGAGCGA CTGTACGCGT TCGGAGCGAA TTTGGACGCC    5100

TCGGAACTGA ATCTGCAGGA CATCAACTCA ATCAAGATTC CACCAACGAC ATGAACCCAA    5160

ATGATGCAGG CAACGCCAAG ACCATTCAGT TCCAACTAAC GAAACGAGGG CATTATATGC    5220

CTGAGGCGTC AATCCGTGTT CGAAATGACA ATGCGACGTC TTATGGACCG GTCGATGAAG    5280

ACACCGAGGA CAACTGTGGT AGATTACACC GGGCAATTGG TGCACTCCAA GGATACCATC    5340

GACAGCAACT TCGCGATAGG TTGCCGTCGA TGACCGGTAT GTCTACATCA ACCGTACCCT    5400

ACTTGCAAGG TGTTCCGACG CTTCGAAGCG ATACCGGCGG AGGGGAGCCT TGGGGCCCCT    5460

TCGCTAGTGC GACACCTCCG AAGGACGACG TGGCGCTAAC AGTGGCTCGA ACTTGGACCG    5520

ATCTGCACCC ATTCGCATAC CCGGAACGAT ACAACGGATT CGGGGCCCTA TTCGCGATGG    5580

TGGCCAAGAC CATAGCCCAG ATACCTCGCT ATGTGCGATC AGCAGCCGGA GTGGCGAATG    5640
```

```
CGGTGACGGA CTGCATAGAG AGCGCGACCG AGAGTGTAGC CTCGAATTCC ACCTCGGAGA      5700

GGCGGCAACG AAGAGCGAGA CGTGTTGGCG GAATCGCTCG AGGAGCCCGC AATCTTGTGG      5760

GCCGCATAGG GAACCTTAGC TTGTAGGTTC ATTGCGACAT GGGATGTTCT TCAGTCAGCA      5820

GCTCTTCGGT TTCATCTCCA CTGACGACCC TCTGCACGTA TTTTCCCATC ATCGTGGTGC      5880

TGATCATCAT TTGCGGTCTG GTTTGGCTCG CTTCCTATTG TTTTCATGGC AGATCAACTC      5940

GACCCAATCG AAATCTTCAT CGAATTCCTC GGATTTCGAA AGATTTCCGG AGCCATTCGC      6000

TGCTTCCAGT GTAAGCAAGT CTTGGGACCT GCAGGACCCG TGGATTCCCA CCTCACTGAT      6060

TGTCAGTGGA AGGCCGCGGT GTTAAATCTT ATTAACAATC AGCTTTACGA CGTCGATATC      6120

GATGAGACGA ATCCGTTTCT TTACGGACCT CACCGCGACT GAGATGTGGA AGACCACATT      6180

GTTCCTTCAC ACATGCCCAG AGTGCGGTTA TTCCACCAGG GACACAGAAA CTACGAGATC      6240

GTGTCCCCGA GATTGCCAAG ACGGCAATCT TATGCACGCA TCTTCGGTCG GCTATATTTG      6300

TCACAAATGC CGGTTAGAAG CAAACACATT TTACCACGGT TTATGCTCTC AGTGTCGCGA      6360

CCGTGATAAT AAAAAACGAC GCTGAAGAGA GGACTCACAA CTACCTCGAT CTCGTTTATC      6420

GGACGAGTGA TACAATTGAC CCAGGGTCAT CCTGCAAAAC ACGCAGGTTT CCGATAGTGG      6480

TGCAAATCCA CCCGCCAGTC GTCGGTGGTC CCTTGCGGGA CCTATACGGT ACCA           6534
```

(2) INFORMATION FOR SEQ ID NO:5:

(i) SEQUENCE CHARACTERISTICS:
        (A) LENGTH: 1233 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Glu Asp Ala Ser Lys Gln Leu Arg Val Leu Asp Ala Gln Glu Arg
 1               5                  10                  15

Ala Lys Ala Ala Phe Gln Leu Asp Phe Ile Ala Ser Val Glu Thr Leu
            20                  25                  30

Glu Asp Ala Gln Glu Lys Tyr Glu Gly Met Met Phe Arg Ser Gly Thr
        35                  40                  45

Lys Leu Pro Ser Thr His Ile Lys Leu Ala Ile Asp Leu Arg Val Ala
    50                  55                  60

Glu Lys Asp Leu Arg Arg His Val Lys Asn Val Pro Thr Val Leu Glu
65                  70                  75                  80

Ile Gly Pro Ser Val Glu Ser Val Arg Tyr Ala Val Gln Thr Arg Asp
                85                  90                  95

Lys Glu Arg Val His Gly Cys Thr Phe Ser Asp Ala Arg Asp Asn Leu
            100                 105                 110

Arg His Asn Lys Ile Gly Tyr Glu Ala His Tyr Asp Arg Lys Ile Gly
        115                 120                 125

Pro Asp Ala Ala Leu Leu Ala Ala Gly Ile Pro Thr Asp Thr Phe Cys
    130                 135                 140

Val Asp Gly Phe Ser Asn Cys Glu Tyr Gln Ser Pro Leu Ala Ile Ala
145                 150                 155                 160

Cys His Ser Leu Tyr Pro Asp Gly Glu Ser Asn Ser Ile Met Asp Val
                165                 170                 175

Ala Lys Gly Met Ala Leu His Gly Thr His Val Ile Tyr Ala Trp Met
            180                 185                 190
```

```
His Leu Pro Val Glu Leu Leu Thr Leu Thr Asp Ala Asp Asn Ile Phe
        195                 200                 205
Glu Gly Tyr Ser Ile Arg Phe Glu Thr Gly Ala Leu Pro Cys Thr
    210                 215                 220
Lys Arg Arg Lys Ala Ile Phe Ser Gly Tyr Asn Asp Phe Gly Ser Ala
225                 230                 235                 240
Tyr Val His Asp Ala His His Trp Ala Gly Trp Lys His Arg Gly
            245                 250                 255
Val Asp Thr Pro Tyr Gly Phe Ser Ile Leu Ile Asp Ile Gln Gln Arg
            260                 265                 270
Phe Gly Met His Thr Lys Leu Lys Ile Thr Arg Gly His Ser Ser Gly
        275                 280                 285
Ser Ile Thr Thr Val Phe Pro Leu Ser Lys Leu Gly Leu Ile Trp Val
    290                 295                 300
Pro Asn Ile Val Lys Ile Met Tyr Pro Lys Ala Lys His Glu Pro Glu
305                 310                 315                 320
Tyr Ile Val Thr Asp Lys Lys Tyr Glu Gly Val Cys Val Tyr Val
            325                 330                 335
Gly Thr Arg Val Gln Ser Ser Gly Lys Ser Ile Thr Leu Ala Glu Ile
            340                 345                 350
Val Gln Tyr Ile Arg Thr Arg Leu Thr Arg Ile Ile Leu Asn Gly Thr
        355                 360                 365
Val His Glu Lys Thr Trp Thr Ile Ala Glu Gln Asp Ile Glu Arg Leu
        370                 375                 380
Ala Val Ser Ile Met Phe Arg Lys Asn Val Glu Arg Ala Val Ser Glu
385                 390                 395                 400
Lys Ala Leu Met Arg Ala Gln Lys Lys Cys Lys Ser Ala Glu Lys Gln
            405                 410                 415
Ala Leu Leu Pro Val Trp Met Arg Arg Ile Ala Asn Trp Phe Gln Asp
            420                 425                 430
Lys Phe Gln Ile Asp Glu Glu Val Val Arg Lys Arg Tyr Leu Glu Cys
        435                 440                 445
Leu Lys Ala Gln Pro Trp Ile His Ala Asp Lys Val Val Asn Cys Glu
    450                 455                 460
Thr Lys Arg Tyr Asn Pro Thr Val Ala Glu Val Gly Pro Lys Asn His
465                 470                 475                 480
Leu Leu Ala Thr Thr Gly Leu Arg Glu Leu Gln Arg Glu Ile Pro Ser
            485                 490                 495
Ala Asn Glu Pro Gln Asp Arg Gly Ala Lys Ala Trp His Ser Ala His
            500                 505                 510
Ala Asp Leu Asp Ile Tyr Ala Glu Gly Leu Arg Leu Asp Ser Ala Lys
        515                 520                 525
Glu Ala Ala Ala Gly Lys Gln Ser Leu Ala Ile Thr Leu Gln Gln Ala
        530                 535                 540
Phe Gln Val Leu Gly Lys Thr Lys Cys Glu Gly Cys Asn Asn Ile Glu
545                 550                 555                 560
Ile Glu Tyr Trp Thr Gly Pro Pro Gly Ser Gly Lys Ser Arg Ala Ala
            565                 570                 575
Lys Pro Arg Phe Ala Asp Leu Gln Gly Gly Val Leu Tyr Cys Ala Pro
            580                 585                 590
Thr Arg Thr Leu Arg Asp Ala Leu Asp Glu Ser Val Val His Pro Ser
        595                 600                 605
```

```
Arg Val Cys Thr Tyr His Asn Ala Leu His Val Ala Lys Glu Ser
    610                 615                 620

Gly Asn Arg Pro Phe Asp Val Ile Val Ile Asp Glu Ala Glu Thr Thr
625                 630                 635                 640

Pro Ala Cys Tyr Val Gly Thr Met His His Ala Ser Pro Ser Ser Arg
                645                 650                 655

Ile Val Cys Leu Gly Asp Pro His Gln Ile Gly Tyr Ile Asp Phe Ser
                660                 665                 670

Asp Arg Lys Asp Asp Leu Lys Pro Phe Ser Ile Ile Ala Ala Glu Cys
            675                 680                 685

Arg Thr Arg Arg Phe Asn Thr Thr Tyr Arg Cys Pro Gln Asp Val Leu
            690                 695                 700

Asn Leu Pro Ile Phe Lys Thr Leu Tyr Pro Asp Ala Ile Ser Phe Ser
705                 710                 715                 720

Lys Gln Leu Thr Ser Ile Arg Tyr Leu Thr Arg Ala Arg Ser Val Thr
                725                 730                 735

Arg Thr Arg His Ala Gln Thr Leu Thr Gln Asp Gln Lys Pro His Ser
            740                 745                 750

Glu Pro Pro Val Thr Ala His Glu Pro Gln Ala Arg Arg Thr Asp Val
    755                 760                 765

Ile Val His Tyr Ala Gly Thr Leu Pro Glu Arg Ala Leu Leu Glu Lys
    770                 775                 780

Val Arg His Ile Asn Val Ala Leu Thr Arg His Thr Asn Ala Leu Tyr
785                 790                 795                 800

Ile Arg Asp Glu Ser Glu Lys Gly Glu Leu Val Pro Ser Leu Met Thr
                805                 810                 815

Pro Pro Ser Trp Ser Thr Tyr Arg Cys Thr Pro Val Asp Lys Gln Met
                820                 825                 830

Val Pro Asp Pro Val Ala Val Glu Arg Glu Asn Gly Ser Ser Gly Pro
            835                 840                 845

Cys Asp Ser His His Ile Gly Ala Ile Thr Ile Leu Gln Glu Leu Gly
    850                 855                 860

Lys Leu Thr Asp Thr Lys Gly Val Arg Val Phe Glu Ser Glu Ala Val
865                 870                 875                 880

Pro Thr Ala His Arg Arg Val Val Leu Asp Gly Asn Leu Asp Ser Gly
                885                 890                 895

Pro Asp Arg Tyr Pro Met Tyr Gln Phe Thr Asn Leu Arg Gly Thr Lys
            900                 905                 910

Tyr Thr Asn Ile Lys Asp Asn Gln Gln Ala Leu His Thr Leu Val Gly
            915                 920                 925

Arg Tyr Ala Arg Lys Ile Asn Ser Ser Ser Arg Glu Thr Pro Ser Leu
    930                 935                 940

Thr Leu Arg Glu Ser Gln Pro Ala Gln Glu Trp Ile Pro Phe Arg His
945                 950                 955                 960

Ala Glu Pro Glu Gln Val Asp Ser Cys Phe Ala Thr Pro Cys Lys Arg
                965                 970                 975

Cys Glu Arg Gly His Gly Val Asp Asp Ile Glu Asp Phe Trp Ser Asn
            980                 985                 990

Glu Gly Gln Arg Ile Ser Tyr His Leu Lys Gly Gln Lys Val Met
    995                 1000                1005

Asp Pro Thr Lys Leu Lys Leu Gly Gln Gly Ile Ser Ala His Glu Lys
    1010                1015                1020

Cys Ala Asn Ile Ala Leu Ser Ala Trp Val Arg Ile Ile Gln Asp Gln
```

-continued

```
1025                1030                1035                1040

Met Ser Thr Ser Glu Lys Phe Ile Phe Ala Asn Gly Gln Ser Asp Arg
                1045                1050                1055

Asp Thr Met Ser Ile Ile Glu Ala Arg Leu Gln Glu Lys Ala Arg Glu
                1060                1065                1070

Phe Lys Ser Ile Asp Ile Lys Glu Phe Asp Thr Val His Asn Trp Val
                1075                1080                1085

Ser Ile Leu Val Phe Ser Trp Arg Cys Asp Arg Gly Cys Pro Glu His
                1090                1095                1100

Leu Ile Glu Tyr Phe Glu Lys Arg Ser Lys Ser Arg Thr Leu Ser Ser
1105                1110                1115                1120

Arg Ile Gly Ser Val Asp Val Ser Phe Met Leu Asp Ser Gly Ala Val
                1125                1130                1135

Trp Thr Ile Ala Arg Asn Thr Leu Phe Ala Ser Gly Leu Met Leu Ala
                1140                1145                1150

Leu Phe Val Gly Val Asp Phe Ile Ala Ala Lys Gly Asp Asp Val Phe
                1155                1160                1165

Leu Ala Gly Asn Asn Leu Tyr Leu Asp Ala Glu Arg Leu Arg Met Gly
                1170                1175                1180

Ser Tyr Leu Ala Ala Asn Asn Leu Lys Ile Glu Lys Thr Ala Val Val
1185                1190                1195                1200

Ser Phe Ile Gly Phe Ile Val Ser Gln Ala Ala Val Thr Ala Asp Val
                1205                1210                1215

Val Arg Leu Ala Thr Arg Thr Tyr Gly Arg Ser Tyr Lys Asn Val Met
                1220                1225                1230

Ile
```

(2) INFORMATION FOR SEQ ID NO:6:

(i) SEQUENCE CHARACTERISTICS:
        (A) LENGTH: 634 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Ser Asp Leu His Leu Asp Pro Gly Phe Val Met Arg Val Thr Pro
1               5                   10                  15

Met Lys Val Asp Glu Arg Val Tyr Ser Gly Gln Asp Gly Cys Gln Arg
                20                  25                  30

Ala Asp Lys Thr Arg Glu Lys Gln Pro Glu Pro Arg Ala Thr Arg Ala
                35                  40                  45

Ala Gln Thr Thr Thr Thr Thr Ser Thr Gln Glu Ala Gly Ser Lys Thr
                50                  55                  60

Ser Pro Arg Ser Arg Thr Asp Tyr Gln Pro Ala Arg Trp Pro Asn Pro
65                  70                  75                  80

Glu Pro Arg Glu His Pro Gly Gln Pro Arg Ser Asp Thr Arg Glu Gly
                85                  90                  95

Ala Lys Ala Ser Asp Asp Gly Glu Ser His Gly Ser Asp Ile Lys Ala
                100                 105                 110

Trp Ile His Asp Tyr Leu Asp Pro Asp Gly Glu Tyr Lys Thr Ser Leu
                115                 120                 125

Asp Asp Gly Lys Ile Pro Asp Gly Ala Ile Pro Gln Ser Thr Cys Gly
                130                 135                 140
```

-continued

```
Gln Phe Arg Gly Thr Val Gly Ala Arg Tyr Pro Gly Leu Asn Ser Thr
145                 150                 155                 160
Thr Leu Pro Leu Asp Gly Gly Thr Trp Pro Leu Leu Val Met His Leu
            165                 170                 175
Pro Phe Phe Arg His Pro Leu Leu Phe Ile Thr Thr Thr Ser Asn Thr
            180                 185                 190
Glu Val Glu Val Thr Asn Ala Asp Leu Asp Ala Phe Ala Asn Asp Trp
            195                 200                 205
Asn Asn Arg Thr Asp Trp Thr Glu Ala Thr Tyr Pro Ser Trp Ala Gln
210                 215                 220
Val Gly Asn Val Phe Tyr Met Val Val Pro Thr Glu Ala Leu Thr Asp
225                 230                 235                 240
Val Pro Pro Thr Gln Leu Gly Val Ser Gly Leu Leu Glu Ser Tyr
                245                 250                 255
Arg Leu Thr Ser Ser Gly Val Thr Ala Tyr Phe Asn Ala Pro Thr Leu
                260                 265                 270
Val Asn Gln Gly Val Ala Val Ile Ala Gln Phe Gln Pro Asp Lys Glu
                275                 280                 285
His Gln Lys Glu Asn Pro Asp Ile Val Ala Gly Thr Thr Gln Thr Gly
    290                 295                 300
Gly Thr Leu Gln Leu Gly Gly Ser Gly Pro Asn Tyr Thr Leu Thr Met
305                 310                 315                 320
Thr Ile Gly Asp Gln Val Glu Phe Gly Ala Ala Ile Pro Leu Pro
                325                 330                 335
Thr Val Ser Met Gly Pro Met Pro Glu Ser Gly Gln Leu Val Phe Gln
                340                 345                 350
Thr Ala Asn Leu Thr Phe Asp Val Gly Asn Thr Ile Thr Ile Thr Thr
                355                 360                 365
Thr Leu Pro Pro Gly Ser Val Thr Gly Met Trp Gln Phe Thr Ala Ser
    370                 375                 380
Asn Gly Thr Asp Thr Val Thr Val Asp Ala Gly Ala Thr Val Arg Val
385                 390                 395                 400
Arg Ser Glu Phe Gly Arg Leu Gly Thr Glu Ser Ala Gly His Gln Leu
                405                 410                 415
Asn Gln Asp Ser Thr Asn Asp Met Asn Pro Asn Asp Ala Gly Asn Ala
                420                 425                 430
Lys Thr Ile Gln Phe Gln Leu Thr Lys Arg Gly His Tyr Met Pro Glu
    435                 440                 445
Ala Ser Ile Arg Val Arg Asn Asp Asn Ala Thr Ser Tyr Gly Pro Val
    450                 455                 460
Asp Glu Asp Thr Glu Asp Asn Cys Gly Arg Leu His Arg Ala Ile Gly
465                 470                 475                 480
Ala Leu Gln Gly Tyr His Arg Gln Gln Leu Arg Asp Arg Leu Pro Ser
                485                 490                 495
Met Thr Gly Met Ser Thr Ser Thr Val Pro Tyr Leu Gln Gly Val Pro
                500                 505                 510
Thr Leu Arg Ser Asp Thr Gly Gly Glu Pro Trp Gly Pro Phe Ala
                515                 520                 525
Ser Ala Thr Pro Pro Lys Asp Asp Val Ala Leu Thr Val Ala Arg Thr
    530                 535                 540
Trp Thr Asp Leu His Pro Phe Ala Tyr Pro Glu Arg Tyr Asn Gly Phe
545                 550                 555                 560
```

```
Gly Ala Leu Phe Ala Met Val Ala Lys Thr Ile Ala Gln Ile Pro Arg
                565                 570                 575

Tyr Val Arg Ser Ala Ala Gly Val Ala Asn Ala Val Thr Asp Cys Ile
                580                 585                 590

Glu Ser Ala Thr Glu Ser Val Ala Ser Asn Ser Thr Ser Glu Arg Arg
                595                 600                 605

Gln Arg Arg Ala Arg Arg Val Gly Gly Ile Ala Arg Gly Ala Arg Asn
    610                 615                 620

Leu Val Gly Arg Ile Gly Asn Leu Ser Leu
625                 630
```

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATGACTCTTC TCTGTGTGGT GGCGATCGGA GTAAG                      35

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGTACTCTTC AACTACCGCT GCTTCTAATC GCAG                       34

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AGTACTCTTC GCAGTACGAC GTCAGCGAGG CCGAC                      35

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATGACTCTTC GAGTCTCTAA GAGCGTGTTC CTAAA                      35

(2) INFORMATION FOR SEQ ID NO:11:

(i) SEQUENCE CHARACTERISTICS:
        (A) LENGTH: 5 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Ser Gly Ser Gly Ser
1               5

(2) INFORMATION FOR SEQ ID NO:12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

CTGCGGTAGG CTAGTCGGGG T                                              21

(2) INFORMATION FOR SEQ ID NO:13:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

AGTGGAAGTG GCACTACTCG ACCCTCCTCT CGTAGG                              36

(2) INFORMATION FOR SEQ ID NO:14:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Ala Thr Thr Phe Ala
1               5

(2) INFORMATION FOR SEQ ID NO:15:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

ACTCGACCCT CCTCTCGTAG G                                              21

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single (D) TOPOLOGY: linear (ii) MOLECULE TYPE: DNA (genomic)

(xi) SEQUENCE DESCRIPTION: SEQ ID NO:16:

AGAAGAAACC AACGGCGT                                             18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AGGACGTTGC CTCCGACTTC                                           20

(2) INFORMATION FOR SEQ ID NO:18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AGTACTCTTC GCAGAGTATG AGTAAAGGAG AAGAACTT                       38

(2) INFORMATION FOR SEQ ID NO:19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

ATGACTCTTC GAGTACTGCC ACTTCCACTT TTGTATAGTT CATCCATGCC          50

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GGCGGTGGCG GATCGGGCGG T                                         21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:21:

GCCTTTAATT AATGAGGAGA C        21

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

AGTGGCACTA CTCGACCCTC CTCTCGTAGG        30